US012653819B2

(12) United States Patent
Tiberg

(10) Patent No.: US 12,653,819 B2
(45) Date of Patent: Jun. 16, 2026

(54) FORMULATIONS AND TREATMENT METHODS

(71) Applicant: Camurus AB, Lund (SE)

(72) Inventor: Fredrik Tiberg, Lund (SE)

(73) Assignee: Camurus AB, Lund (SE)

( * ) Notice: Subject to any disclaimer, the term of this patent is extended or adjusted under 35 U.S.C. 154(b) by 993 days.

(21) Appl. No.: 17/639,365

(22) PCT Filed: Sep. 1, 2020

(86) PCT No.: PCT/EP2020/074361
§ 371 (c)(1),
(2) Date: Mar. 1, 2022

(87) PCT Pub. No.: WO2021/043771
PCT Pub. Date: Mar. 11, 2021

(65) Prior Publication Data
US 2022/0288061 A1 Sep. 15, 2022

(30) Foreign Application Priority Data
Sep. 2, 2019 (SE) .................................... 1950999.1

(51) Int. Cl.
| | |
|---|---|
| *A61K 31/485* | (2006.01) |
| *A61K 9/00* | (2006.01) |
| *A61K 47/10* | (2017.01) |
| *A61K 47/14* | (2017.01) |
| *A61P 25/36* | (2006.01) |

(52) U.S. Cl.
CPC .......... *A61K 31/485* (2013.01); *A61K 9/0019* (2013.01); *A61K 9/0053* (2013.01); *A61K 47/10* (2013.01); *A61K 47/14* (2013.01); *A61P 25/36* (2018.01)

(58) Field of Classification Search
CPC .. A61K 31/485; A61K 9/0019; A61K 9/0053; A61K 47/10; A61K 47/14; A61P 25/36
See application file for complete search history.

(56) References Cited

U.S. PATENT DOCUMENTS

| | | | |
|---|---|---|---|
| 8,236,292 B2 | 8/2012 | Thuresson et al. | |
| 8,236,755 B2 | 8/2012 | Thuresson et al. | |
| 8,545,832 B2 | 10/2013 | Thuresson et al. | |
| 9,937,164 B2 | 4/2018 | Tiberg et al. | |
| 10,912,772 B2 | 2/2021 | Tiberg et al. | |
| 11,110,084 B2 | 9/2021 | Tiberg et al. | |
| 11,135,215 B2 | 10/2021 | Tiberg et al. | |
| 2020/0375979 A1 | 12/2020 | Tiberg et al. | |

FOREIGN PATENT DOCUMENTS

| | | | |
|---|---|---|---|
| WO | WO-2005/011579 A2 | | 2/2005 |
| WO | WO-2014/016428 A1 | | 1/2014 |
| WO | WO 2016/666655 | * | 5/2016 |
| WO | WO-2017/046384 A1 | | 3/2017 |
| WO | WO-2021/043771 A1 | | 3/2021 |

OTHER PUBLICATIONS

Khodaverdi, E. et al., In-vitro and in-vivo evaluation of sustained-release buprenorphine using in-situ forming lipid-liquid crystal gels, Life Sciences, 314: 121324, pp. 1-11 (2023).
Bishop, Bryan M., Buprenorphine for the Treatment of Neonatal Abstinence Syndrome, Journal of Pharmacy Technology, 34(6):266-272 (2018).
Disher, T. et al., Pharmacological Treatments for Neonatal Abstinence Syndrome—A Systematic Review and Network Meta-analysis, JAMA Pediatrics, 173(3):234-243 (2019).
International Search Report for PCT/EP2020/074361, 5 pages (Dec. 17, 2020).
Kraft, W.K. et al., Buprenorphine for the Treatment of the Neonatal Abstinence Syndrome, N. Engl. J. Med., 376(24):2341-2348 (2017).
Kraft, W.K. et al., Sublingual buprenorphine for treatment of neonatal abstinence syndrome: a randomized trial, Pediatrics, 122(3):e601-7 (2008).
Written Opinion for PCT/EP2020/074361, 7 pages (Dec. 17, 2020).

* cited by examiner

*Primary Examiner* — Sahar Javanmard
(74) *Attorney, Agent, or Firm* — Choate, Hall & Stewart LLP; Charles E. Lyon; Michael A. Shinall

(57) ABSTRACT

A lipid controlled-release formulation comprising: a) about 30 to about 50 wt % of at least one diacyl glycerol; b) about 30 to about 50 wt % of at least one phosphatidylcholine; c) about 5 to about 15 wt % ethanol; d) about 0.05 to about 0.5 wt % buprenorphine. A method for the treatment of neonatal abstinence syndrome (NAS) in a human infant in need thereof, said treatment involving the steps of: administering a controlled-release formulation containing a dose of at least one opioid to said infant; wherein said controlled-release formulation provides a therapeutically effective amount of the at least one opioid for at least 4 days following administration.

14 Claims, 2 Drawing Sheets

FORMULATIONS AND TREATMENT METHODS

FIELD

The present disclosure relates to formulation precursors (pre-formulations) for the in situ generation of controlled release opioid compositions. In particular, the disclosure relates to sustained release compositions and corresponding precursor formulations, containing at least one opioid active agent, especially buprenorphine. The disclosure also relates to the use of such formulation precursors in the treatment of neonatal abstinence syndrome (NAS). The disclosure also relates to a method for the treatment of NAS.

BACKGROUND

Neonatal abstinence syndrome (NAS) refers to the collection of signs witnessed in an infant which are caused by substance or medication withdrawal. The infant may have first been exposed as a foetus during pregnancy, or may have contracted NAS as a result of withdrawal from drugs such as opioids administered to newborns with serious illness. The symptoms of the withdrawal include, but are not limited to, fever, trembling, sleeping problems, agitation, nasal congestion, yawning, diaphoresis, tight muscle tone and cramps, diarrhea, nausea, vomiting, high pitch crying, hyperactive reflexes and seizures.

Neonatal Opioid Withdrawal Syndrome (NOWS) is a subset of NAS and defines a constellation of symptoms that are present in some newborn infants resulting from the abrupt cessation of passive transfer of maternal opioids used during pregnancy. See Gomez-Pomar & Finnegan, *Front Pediatr.*, 6:33 (Feb. 22, 2018). It is estimated that 50 to 80% of infants born from mothers with Opioid Use Disorder (OUD) are diagnosed with NAS and/or NOWS. See Kakko, et al., *Drug Alcohol Depend.*, 96(1-2):69-78 (Jul. 1, 2008); Reddy, et al., *Obstet. Gynecol.*, 130(1):10-28 (July 2017) and most infants with NAS were exposed to multiple substances in utero prior to birth. See Hall, et al., *Pediatrics*, 136(4):e803-10 (October 2015); Hall, et al., *J. Pediatrics*, 170:39-44.e.1 (March 2016); Hall, et al., *Am. J. Perinatol.*, 35(4):405-412 (Epub Nov. 7, 2017). Since the infant may have been exposed to multiple substances in utero, there may be multiple causes of NAS but in treating the symptoms of NAS, the overall health and symptoms of the neonate will generally be improved. This is important since NAS is a serious condition, which may be life-threatening if not treated in the neonate. See Cramton & Gruchala, *Curr. Opin. Pediatr.*, 25(4):532-42 (August 2013)

An infant experiencing NAS generally requires a high degree of care and their discharge from hospital can be prolonged. It has been estimated that in 2009 US hospital charges associated with NAS were between 640-800 million US dollars (Patrick et al., *Neonatal Abstinence Syndome and Associated Health Care Expenditures* IAMA 2012; 307(18): 1934-1940).

In case of occurrence of mild withdrawal symptoms in the newborn infant, frequent feedings, decreased stimulation and swaddling is beneficial. A similar regime involves low stimulation, parental engagement and/or breast-feeding. This type of care, sometimes termed Eat, Sleep, Console (ESC), may be sufficient in some cases and is appropriate even where other treatments are also necessary. For more severe cases, and in the event of excessive weight loss, significant vomiting and/or diarrhea, infants are treated with a number of medications which may include opioids.

There are a variety of treatments currently available for infants experiencing NAS: pharmacologic therapy is normally recommended for infants with high scores in the NAS scoring methods described below. Short-acting opioids such as morphine sulphate are restricted to hospitalized infants who must be weaned before discharge whereas long-acting opioids such as methadone may be continued and the infant weaned as an outpatient.

Common treatments for NAS include:

| Medication | Oral Dose |
| --- | --- |
| Morphine | 0.03-0.1 mg/kg q 3 to 4 hr |
| Methadone | 0.05-0.1 mg/kg q 6 to 25 hr |
| Buprenorphine | 5.3 µg/kg q 8 hr |
| Phenobarbital | 1-4 mg/kg q 12 hr |
| Clonidine | 0.5-1 µg/kg q 4 to 6 hr |

See Siu et al., *J Pediatr. Pharmacol. Ther.* 19(3): 147-155 (2014).

The table above does not reflect the weaning period required, which can be substantial. Siu et al. notes that while buprenorphine does not require the same length of treatment as other opioids, treatment was still required for 23 days on average for infants given sublingual buprenorphine. *J Pediatr. Pharmacol. Ther.*, 19(3): 147-155 (2014).

Despite the recommendations of the American Academy of Pediatrics for standardization of NAS treatment, there is significant variation in pharmacologic treatment choices, strengths, dosing regimens and protocols across hospitals and between providers. (Grossman 2017, Hudak 2012, Bogen 2016, Patrick 2014, Milliren 2018, Wachman 2016, Pham 2017, Kraft 2017). There is thus currently a move to standardise care for NAS/NOWS infants, particularly in the US. However, in other regions, such as Europe, the care protocol for NAS/NOWS infants is often solely the choice of local hospital or practitioner policy.

In view of the above, it would be a considerable advantage to provide a treatment method that can address the symptoms of NAS/NOWS with minimal hospital stay, reduced medical practitioner time and/or minimised disruption to normal mother/baby bonding. It would be a further advantage if such treatment removes or reduces the need for multiple dosages, thus also eliminating the possibility that mothers with a disrupted lifestyle will omit follow-up treatments. There is a need for treatments for infants suffering from NAS that do not require frequent (e.g. hourly, daily) administration of a therapy to such an infant

Definitions

The term "infant" means a human child between the ages of newly born to 3 months. In some embodiments, an infant is a neonate of age 1 month or less (i.e. newborn to 1 month of age).

The term "NAS scoring method" is any method used to correlate the infant's condition to a NAS score. Where a specific NAS scoring method is referred to this is clearly indicated. Any of the NAS/NOWS scoring methods described herein may be applied unless otherwise indicated. Exemplary NAS/NOWS scoring methods include the Finnegan scoring method and the "modified" Finnegan scoring method. A NAS score allows practitioners to assess and identify the withdrawal symptoms, document the infant's withdrawal, and initiate the appropriate treatment regimen, when needed. An elevated score indicates a clinically significant withdrawal, and that an infant might be a candidate for pharmacologic treatment.

The term "controlled-release formulation" indicates a formulation which provides controlled release of an active agent over an extended period of time. This will generally provide a therapeutically effective amount (i.e. a blood plasma concentration of active agent within the therapeutic window) for a period of at least 4 days (e.g. 5-30 days). For use in all aspects of the present disclosure, the controlled-release formulation will release at least one opioid active agent. For use in all aspects of the present disclosure, the controlled-release formulation will generally be administered by injection.

A "lipid controlled-release formulation" as used herein is a controlled-release formulation having a lipid controlled-release matrix which forms a controlled-release "depot" upon administration. Such formulations are described herein and may be formulated with one or more lipid components in addition to an opioid active agent.

An infant "in need of treatment" for NAS/NOWS is used herein to indicate an infant diagnosed with NAS, or NOWS. Such diagnosis may be the result of showing signs of withdrawal symptoms or by factors such as maternal history of opioid use. Diagnosis by signs and symptoms of withdrawal may be by any appropriate "NAS scoring method". Many such methods are described herein.

The term "opioid" includes natural and synthetic opioids, opioid agonists or opioid antagonists. In some embodiments, an opioid, opioid agonist, or opioid antagonist is selected from morphine, methadone and buprenorphine. In some embodiments, an opioid, opioid agonist, or opioid antagonist is buprenorphine.

As used herein, all figures, including those with one or more zero in the least significant places, are intended to be significant to all digits quoted, including such zeros. Thus, for example, "100" as indicated herein is intended to mean $1.00 \times 10^2$ and not simply $1 \times 10^2$. Correspondingly, all integer numbers, including those ending in zero(s), may be taken as ±0.5.

As used herein, the term "about", "around", "substantially" or "approximately" in relation to a number or a range of numbers will generally indicate that the number or range specified is preferred but that such a number may be varied to a certain extent without materially affecting the properties of the relevant material, composition or similar product. The skilled worker will typically be able to readily establish the extent by which such numbers may be varied without prejudicing the key advantages of the present disclosure. As a general guide, such numbers or the ends of such ranges may be varied by ±10%, ±5%, ±1%, ±0.5%, or ±0.2% with respect to any given number.

The term "alkyl", used alone or as part of a larger moiety, refers to a saturated, optionally substituted straight or branched chain or cyclic hydrocarbon group having (unless otherwise specified) 1-12, 1-10, 1-8, 1-6, 1-4, 1-3, or 1-2 carbon atoms (e.g. $C_1$-$C_{12}$, $C_1$-$C_{10}$, $C_1$-$C_8$, $C_1$-$C_6$, $C_1$-$C_4$, $C_1$-$C_3$, or $C_1$-$C_2$). Exemplary alkyl groups include methyl, ethyl, propyl (e.g. n-propyl, isopropyl), butyl (e.g. n-butyl, sec-butyl, isobutyl, t-butyl, etc.), pentyl, hexyl, and heptyl.

The term "alkenyl", used alone or as part of a larger moiety, refers to an optionally substituted straight or branched chain or cyclic hydrocarbon group having at least one double bond and having (unless otherwise specified) 2-12, 2-10, 2-8, 2-6, 2-4, or 2-3 carbon atoms (e.g. $C_2$-$C_{12}$, $C_2$-$C_{10}$, $C_2$-$C_8$, $C_2$-$C_6$, $C_2$-$C_4$, or $C_2$-$C_3$). Exemplary alkenyl groups include ethenyl, propenyl, butenyl, pentenyl, hexenyl, and heptenyl.

The term "acyl," as used herein, is a subset of a substituted alkyl group, and refers to a group having the general formula —$C(O)R^4$, —$C(O)OR^4$, wherein $R^4$ is hydrogen; halogen; or substituted or unsubstituted alkyl or alkenyl moiety.

A corresponding meaning may be attributed to compositions "consisting essentially of" certain components, which may include up to 10%, preferably up to 5% and most preferably up to 1% of other components in addition to those specified.

As used herein "opioid" or a specific opioid such as buprenorphine refers to the free base and to salts thereof. Such salts will be pharmaceutically acceptable salts and many such salts are known in the art. Where a mg/mL or mg/g value is indicated for an opioid (e.g. buprenorphine), this relates to the weight of free base drug or the corresponding weight where a salt is used, corrected for the additional molecular weight (MW) of the salt. In general terms, the amount of salt to be included will correspond to:

$$\text{Weight of salt to use} = \text{Desired weight of free base} \times \text{MW of salt/MW of free base}$$

Thus, for example, 0.50 mg/g in a formulation may correspond to 0.50 mg of buprenorphine (MW 467.6) in a gram of formulation or to 0.539 mg of buprenorphine hydrochloride (MW 504.1). This is calculated as $0.50 \times 504.1/467.6 = 0.539$.

A deviation from the above definitions is possible where context permits or requires.

SUMMARY

The present disclosure encompasses the insight that certain formulations are useful for the treatment of infants suffering from NAS by providing particular therapies in a controlled release, injectable formulation.

In a first aspect herein is provided a lipid controlled-release formulation comprising:
   a) 30-50 wt % of at least one diacyl glycerol;
   b) 30-50 wt % of at least one phosphatidylcholine;
   c) 5 to 15 wt % ethanol;
   d) 0.05 to 0.5 wt % buprenorphine.

In some embodiments, a controlled-release formulation comprises a ratio of components a):b) of 40:60 to 60:40. In some embodiments, a controlled-release formulation comprises a ratio of components a):b) of 45:55 to 55:45.

In some embodiments, a controlled-release formulation comprises a proportion of the sum of the weights of components a) and b) to the total weight of the formulation of at least 50% (e.g. 50 to 95%). In some embodiments, a controlled-release formulation comprises 50% by weight or greater of components a) and b) (i.e. a combined weight of component a) and b) make up 50% or more (e.g. up to 95%, or, 97%, or 98%, or 99%) of the weight of a controlled-release formulation).

In a second aspect herein is provided a controlled-release formulation as indicated herein, for example a controlled-release formulation comprising components a) to d) as indicated herein, for use in the treatment of Neonatal Abstinence Disorder (NAS) in an infant. In particular, NAS may be or may comprise neonatal opioid withdrawal syndrome (NOWS). In some embodiments, a controlled-release formulation is used in a method comprising administration to an infant having been diagnosed with NAS or NOWS, as discussed herein) by injection. In some embodiments, an infant is a neonate (i.e. an infant of age 1 month or less, for example, an infant of age 1 month or less). In some embodiments, a controlled-release formulation provides 25-500 μg of buprenorphine per kg of body weight of a neonate.

In some embodiments, the present disclosure provides a method of treating an infant (e.g., a neonate) suffering from NAS, the method comprising administering a controlled-release formulation comprising:

a) about 30 to about 50 wt % of at least one diacyl glycerol;

b) about 30 about 50 wt % of at least one phosphatidyl-choline;

c) about 5 to about 15 wt % ethanol;

d) about 0.05 to about 0.5 wt % buprenorphine.

In some embodiments, the present disclosure provides a method of treating an infant (e.g., a neonate) suffering from NAS, the method comprising administering a controlled-release formulation comprising:

a) 30 to 50 wt % of at least one diacyl glycerol, e.g. glycerol dioleate;

b) 30 to 50 wt % of at least one phosphatidylcholine;

c) 5 to 15 wt % ethanol;

d) 0.05 to 0.5 wt % buprenorphine.

In a third aspect herein is provided a pre-filled vial containing a formulation as indicated herein. In some embodiments, a pre-filled vial comprises a controlled-release formulation comprising components a) to d) as indicated herein. In some embodiments, a pre-filled vial comprises a controlled-release formulation described herein in an amount of 0.1 to 1 mL (e.g., 0.2 to 0.5 mL). In some embodiments, a pre-filled vial comprises a controlled-release formulation described herein in an amount of about 0.5 mL.

In a fourth aspect herein is provided a method for the treatment of neonatal abstinence syndrome (NAS) in a human infant in need thereof (e.g. diagnosed with NAS as described herein), said treatment comprising:

administering a controlled-release formulation containing a dose of at least one opioid (such as buprenorphine) to said infant;

wherein said controlled-release formulation provides a therapeutically effective amount of opioid for at least 4 days (preferably 5 to 21 days) following administration.

BRIEF SUMMARY OF THE ATTACHED FIGURES

DETAILED DESCRIPTION

Figure 1:
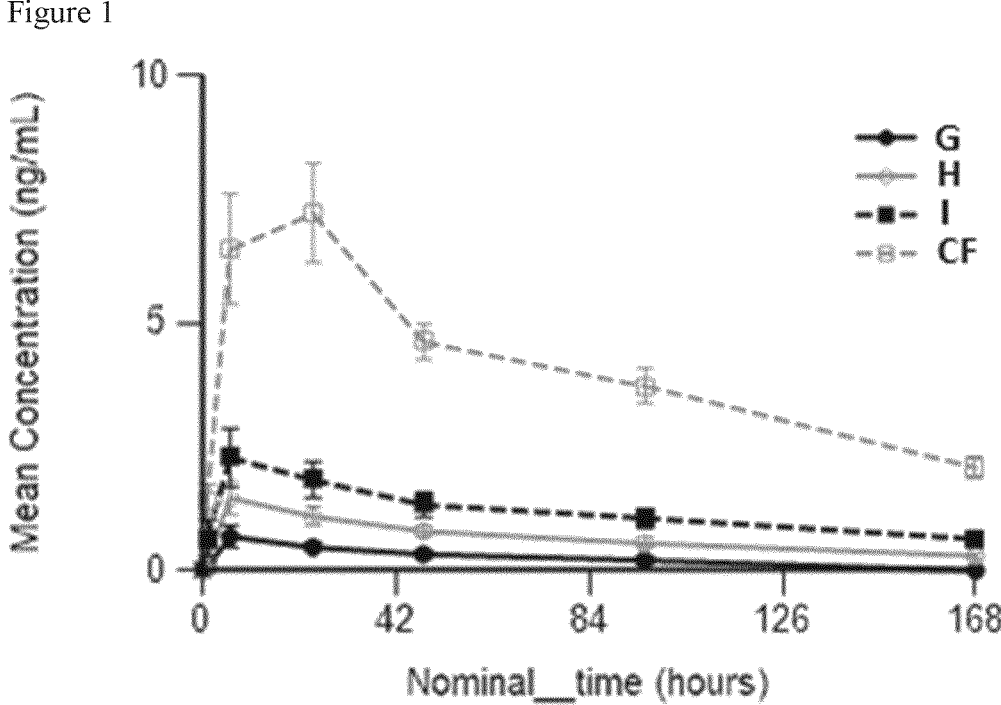
FIG. 1 shows mean Plasma Concentrations of BUP in Animals of Treatment Groups 1-4; hours 0-168 (Linear Scale).

Neonatal abstinence syndrome is a growing problem, with the incidence in infants increasing dramatically over the past 15 years. See Siu et al., *J Pediatr Pharmacol Ther.* 2014; 19(3): 147-155 (2014). Opioid misuse during pregnancy affects more than 5% of all pregnant women in the United States. See Davis et al., *JAMA Pediatrics,* 172(8): 741-748 (2018). Withdrawal symptoms are seen in about 80% of neonates exposed to opioids in utero. See Kushnir et al., *Pediatrics,* 146(1 Meeting Abstract): 118-119 (2020).

Most forms of treatment for NAS require daily, if not hourly administration of a particular therapy. There is a need for treatments for infants suffering from NAS that do not require frequent (e.g. hourly, daily) administration of a therapy to such an infant. The present disclosure encompasses the insight that certain formulations are useful for the treatment of infants suffering from NAS by providing particular therapies in a controlled release, injectable formulation.

The disclosure is described below in detail with respect to formulation and method of treatment aspects of the disclosure. However, all features are to be understood as being disclosed in the context of all aspects, including the purpose-limited formulations according to the disclosure and all other aspects which are technically compatible.

Methods of Treatment

Current pharmacological treatment for NAS/NOWS is inconsistent between countries and hospitals. Current best practices typically includes Eat, Sleep, Console (ESC) type comforting of the infant with more severe cases also receiving either a short-acting opioid or a long-acting opioid. The barbiturate phenobarbital may also be used, with or without an opioid. The methodology for a typical current pharmacological treatment method is given as Comparative Example 2. To calculate the dosage, there are a variety of factors to be considered:

the infant's gestational age, general health, and medical history the extent of NAS based upon NAS scores the infant's tolerance for specific medications, procedures or therapies expectations for the course of the disease the guardian's opinion or preference such as for certain drugs Current treatments, however, require frequent administration of an opioid. The present disclosure encompasses the insight that certain formulations are useful for the treatment of infants suffering from NAS by providing particular therapies in a controlled release, injectable formulation.

The various aspects of the present disclosure relate to administration of a controlled-release, injectable formulation of an active agent, for example, an opioid. Opioids are well known active agents in the art and some opioids are used in the current standard of care for infants with NAS/NOWS. Use of morphine in treatment of NAS is common, as is the use of methadone, which has been shown to provide a decreased Length of Stay in hospital (LOS) in comparison with morphine. See Davis et al., *JAMA Pediatrics,* 172(8): 741-748 (2018). Buprenorphine has been shown to reduce treatment duration in comparison with methadone. Hall, et al., *Am. J Perinatol.,* 35(4):405-412 (Epub Nov. 7, 2017). Usable formulations of buprenorphine, however, are often not readily available. The standard buprenorphine formulations are sublingual and cannot readily be applied to neonates. They must therefore be specially compounded for application as a solution under the tongue, which introduces the risk of compounding and application errors. The present disclosure is well suited to address the problems indicated above.

In some embodiments, the present disclosure provides a method for the treatment of neonatal abstinence syndrome (NAS). In some embodiments, the present disclosure provides a method of treating a patient (e.g. an infant) suffering from a neonatal abstinence syndrome comprising:

administering to the patient a controlled-release formulation comprising at least one opioid;

wherein the controlled-release formulation provides a therapeutically effective amount of the opioid for at least 4 days following administration.

In some embodiments, the present disclosure provides a method of treating a patient (e.g. an infant) diagnosed with one or more symptom(s) of neonatal abstinence syndrome comprising:

administering to the patient a controlled-release formulation comprising at least one opioid;

wherein the controlled-release formulation provides a therapeutically effective amount of the opioid for at least 4 days following administration.

In some embodiments, and as described generally herein, a controlled-release formulation is administered by injection (e.g. parenterally such as by subcutaneous injection). For example, in some embodiments, a controlled-release formulation described herein is administered subcutaneous (e.g., is injected into a subcutaneous tissue). In some embodiments, a controlled release formulation is administered to a subcutaneous tissue selected from the buttocks, the thigh, the abdomen, and the upper arm.

In some embodiments, a controlled-release formulation provides a therapeutically effective amount of an opioid for 4 to 21 days following administration. In some embodiments, a controlled-release formulation provides a therapeutically effective amount of opioid for 4 to 10 days following administration. In some embodiments, a controlled-release formulation provides a therapeutically effective amount of opioid for 4, 5, 6, 7, 8, 9, or 10 days following administration.

In some embodiments, a patient is administered a controlled-release formulation once per week. In some embodiments, a patient is administered a controlled-release formulation once per week for one or more weeks. In some embodiments, a patient is administered a controlled-release formulation once per week for one to six weeks, such as one to four weeks. In some embodiment, a patient is administered a controlled-release formulation once only. In some embodiments, a patient is administered a controlled-release formulation once, twice, or three times over the course of a treatment cycle (e.g., once per week for one, two, or three weeks).

In some embodiments, an amount (i.e. the dose) of the at least one opioid is decreased for subsequent administrations after the initial administration. In some embodiments, an amount (i.e. the dose) of the at least one opioid is the same for subsequent administrations after the initial administration. In some embodiments, an amount (i.e. the dose) of the at least one opioid is increased for subsequent administrations after the initial administration.

In some embodiments, a controlled-release formulation is administered as two injections or less. In some embodiments, a controlled-release formulation is administered as a single injection, e.g. a subcutaneous injection. This will for example be of a small volume to reduce the discomfort to the infant. In some embodiments, an injection volume for a controlled-release formulation will be 1 mL or less, e.g. about 0.10 mL to about 1 mL, such as 0.10 mL to 1 mL. In some embodiments, an injection volume for a controlled-release formulation is from about 0.1 mL to about 0.5 mL, e.g. 0.1 mL to 0.5 mL. In some embodiments, an injection volume for a controlled-release formulation is from about 0.15 mL to about 0.5 mL, e.g. 0.15 mL to 0.5 mL. In some embodiments, an injection volume for a controlled-release formulation is from about 0.2 mL to about 0.5 mL, e.g. 0.2 mL to 0.5 mL.

In some embodiments, a single injection is administered. In some embodiments, two or more injections are administered. In some embodiments, two injections are administered. In some embodiments, a second injection will occur from about 12 hours to about 5 days after the first injection, such as between 12 hour and 5 days, such as between 18 and 72 hours after the first injection. Such second injection may be made in the event that the initial injection was insufficient to control symptoms of NAS in the infant to a tolerable level. Such insufficiency will typically be determined within 24 hours of the first injection and a second "top-up" injection may be made shortly after such a determination.

In some embodiments, the present disclosure provides a method of treating a patient (e.g. an infant) suffering from a neonatal abstinence syndrome comprising administering to the patient a controlled-release formulation comprising at least one opioid to the patient diagnosed with NAS. In some embodiments, a patient diagnosed with NAS is characterized by one or more factors of an NAS scoring method, described herein. In some embodiments, an NAS scoring method is or comprises a Finnegan, Lipsitz, Ostrea, Rivers, or the Neonatal Intensive Care Unit Network Neurobehavioral Scale. In some embodiments, a patient diagnosed with NAS is characterized by one or more symptoms of NAS, e.g. symptoms exemplified in Comparative Examples 1 and/or 2.

In some embodiments, the present disclosure provides a method of treating a patient (e.g. an infant) suffering from NAS, comprising further administering non-pharmacological methods. In some embodiments, non-pharmacological methods comprise low stimulation, parental engagement and/or breast-feeding. In some embodiments the non-pharmacological methods are in addition to the pharmacological methods disclosed in the present disclosure.

Diagnosis of NAS/NOWS

In some embodiments, NAS is neonatal opioid withdrawal syndrome (NOWS). Diagnosis of NAS/NOWS in an infant may be the result of the infant showing signs of withdrawal symptoms or by factors such as maternal history of opioid use.

Diagnosis by signs and symptoms of withdrawal may be by any appropriate "NAS scoring method". Such scoring methods apply ratings to the clinical signs and symptoms of NAS/NOWS and inform the clinician of appropriate levels of intervention depending upon the score, appropriate thresholds and potentially also the change in score over time.

Clinical signs and symptoms associated with NAS/NOWS which may be used in diagnosis include Central Nervous System (CNS) signs and symptoms; Metabolic, Vasomotor and Respiratory signs and symptoms; and Gastrointestinal signs and symptoms. Typical CNS signs and symptoms that may be taken into account include: excessive, especially continuous, high-pitched crying; sleep disturbances (such as short duration of sleep after feeding e.g. less than 2 hours or less than 1 hour); hyperactive Moro reflex (especially longer than 4 seconds); mild or moderate tremors (especially longer than 3 seconds, either when disturbed or undisturbed); increased muscle tone (e.g. no head lag or arms not straightening when lifted gently by wrists); excoriation (especially with broken skin); myoclonic jerk; and generalised convulsions. Typical Metabolic, Vasomotor and Respiratory signs and symptoms that may be taken into account include: sweating; fever (especially above 38.4° C.); frequent yawning; mottling; nasal stuffiness (e.g. noise when breathing); sneezing (e.g. more than 3 times in 3-4 hours); nasal flaring; and high breathing rate (especially more than 60/min and particularly more than 60/min with chest retractions). Typical Gastrointestinal signs and symptoms that may be taken into account include: excessive sucking; poor feeding (e.g. uncoordinated sucking reflex, small amount taken, frequent pauses in feeding to breathe, feeding time longer than 20 min); regurgitation (especially projective vomiting or vomiting of complete feed); loose and especially watery stools. Other signs and symptoms that may be taken into account include: weight less than 90% of birth weight; excessive irritability (e.g. excessive sensitivity to sound or light, irritability to touching or handling in spite of attempts to console, or infant takes a long period such as more than 5 min or more than 15 min to calm when consoled).

Any one of the above signs and symptoms may be associated with other conditions but at least one sign or symptom will be present in NAS/NOWS and typically a clinician will make a judgement in a specific case that such symptom(s) are associated with NAS. This judgement will generally be aided by a scoring system such as those described herein.

The medical history of the mother may also be taken into account when assessing the likelihood of the infant to have NAS/NOWS because the foetus may have been exposed to the same chemical environment as the mother. In this context, maternal opioid exposure, timing of such exposure and dosage may be treated as a clinical sign of NAS/NOWS in the infant. In one embodiment, maternal opioid exposure, especially within 7 days of delivery of the infant, may be taken as indicating NOWS (and thus NAS). This may be a sole factor or may be combined with other signs and symptoms as described herein and known in the art.

Toxicology testing, such as where biologic specimens from the neonate including meconium, hair, cord blood and/or urine, can be advantageous in identifying substance exposure in the newborn. These tests, however, have limitations which include the timing of sample collection and the length of the period of detection of drug exposure. Similar testing of the mother shortly before or shortly after the birth may also be treated as a sign of NAS/NOWS in the infant, where such testing reveals significant opioid exposure in the mother.

A Neonatal Abstinence Syndrome scoring system is typically used to diagnose and grade the severity of NAS. There are a variety of NAS scoring systems described below, where points are assigned for certain clinical signs and the severity of each. In the current disclosure such scoring may be used in diagnosis of NAS/NOWS. Scoring systems may also be used to help in planning treatment e.g. dosage. The 11 typical clinical signs of NAS used in the Lipsitz scoring method are examples of signs that may be used to indicate the presence of NAS, e.g. see Comparative Example 1. The Finnegan Neonatal Abstinence Scoring Tool (FNAST), including the modified Finnegan Scoring tool, is another suitable scoring tool. See Jansson, et al., *J. Opioid Manag.,* 5(1):47-55 (2009).

At least one factor in the measurement of symptom, clinical sign or other indications of NAS is preferably calculation of the infant's NAS score according to at least one NAS scoring system. The purpose of this step is to establish the presence of NAS and preferably to assess the severity of the symptoms, then to determine whether pharmacological treatment is necessary and optionally what dosage may be appropriate as a starting point for treatment.

A number of different scoring systems have been developed to assess the severity of NAS (mostly considering opiate dependency—NOWS) based on observable clinical signs: Finnegan, "modified" Finnegan, Lipsitz, Ostrea, Rivers and the Neonatal Intensive Care Unit Network Neurobehavioral Scale are common examples, as are the neonatal narcotic withdrawal index, neonatal withdrawal inventory and MOTHERS NAS scale. Any of these or similar systems may be used in the present disclosure as diagnosis of NAS/NOWS or as a contribution towards such diagnosis. These may be employed individually or in combination.

The Finnegan scoring method and "modified" Finnegan scoring method is presently the most widely used. See Jansson, et al., *J. Opioid Manag.,* 5(1):47-55 (2009). This assesses 21 of the most common signs of neonatal abstinence syndromes, scoring the infant on the basis of pathological significance and severity of the adverse symptoms. To obtain a daily average score, measurements are performed by trained personnel every 4 hours until the patient is considered stable. Typically, if 3 consecutive scores are equal to or greater than 8, pharmacological treatment for withdrawal is started. This may be considered "diagnosis of NAS/NOWS" for the purposes of the present disclosure.

In some embodiments, a patient is diagnosed with NAS/NOWS, as described herein, if the patient satisfies one or more of the following criteria (e.g., criteria of the modified Finnegan's scoring system):

Crying (excessive or continuous)
Lack of sleep
Hyperactive Moro reflex
Tremors
Increased muscle tone
Excoriation (e.g. on the chin, knees, elbows, toes, or nose)
Myoclonic jerks
Generalized convulsions
Increased sweating
Hypothermia
Frequent yawning (e.g. 3-4 times per scoring interval)
Mottling
Nasal stiffness
Sneezing (e.g. 3-4 times per scoring interval)
Nasal flaring
Increased respiratory rate (e.g. 60 breaths/minute)
Excessive sucking
Poor feeding
Regurgitation
Projective vomiting
Loose or watery stool In some embodiments, a patient is diagnosed with NAS/NOWS, as described herein, if the patient satisfies one or more of the following criteria (e.g., criteria of the Lipsitz scoring system):

Tremors: involuntary muscle activity of limbs which are rhythmical and normally of equal amplitude, including seizure on the rare occasion.

Irritability: excessive crying, high pitched and with no apparent reason. Inconsolable even after normal comforting measures.

Exaggerated Moro startle reflex even when examined at rest.

Loose, frequent, watery stools which may also be explosive with or without a water ring. Ignore 'breast milk' stools.

Varying degrees of muscle stiffness or rigidity.

Skin abrasions on elbows, heels or other pressure points. Ignore extremities frequently rubbed against bed linens and diaper rash.

Respiratory rate where infant is tachypneic or if breathing is laboured or retractions are present. Count respirations for sixty seconds when the infant is calm or asleep by touch or direct visualization of the chest and/or abdomen.

Repetitive sneezing may be a sign of autonomic nervous system dysregulation.

Repetitive yawning may represent alterations in autonomic nervous system regulation.

Projectile or forceful vomiting or right after baby is fed. Vomiting not necessarily related to burping and occurs frequently during feeding.

Fever >38° C. (>100.4° F.) unrelated to infant being overdressed or because of an infection.

Other factors may also be considered before commencing the treatment such as reported exposure, the age of the infant, whether an inpatient or outpatient strategy is used, consideration of comorbidities and the experience of the clinician who makes treatment decisions.

In some embodiments a NAS scoring system may be used in conjunction with herein disclosed formulations, such as a lipid controlled-release formulation comprising buprenorphine (as disclosed herein including in the attached claims). The severity of NAS in newborns will then be scored against the NAS scoring system and, in one embodiment, a single subcutaneous dose of the lipid controlled-release formulation may be administered accordingly.

The specific method of scoring is not critical and may be an established method or may be developed or modified. Importantly the infant should show one or more signs or clinical symptoms associated with withdrawal, such as opioid withdrawal. Typically the infant will show a range of symptoms which collectively indicate NAS/NOWS of a severity that would benefit from pharmaceutical intervention.

In some embodiments of NAS/NOWS scoring tools, an optional step may be included, after at least one symptom, clinical sign, or other indication associated with NAS or NOWS is measured and before a controlled-release formulation that contains a dose of at least one opioid is administered to the infant. In this optional step, a short-term dose of an opioid may be administered to the infant before measuring their NAS score, to determine the need of opioids before a long-term dose is given to the infant. This may be required by certain practitioners. The optional step may be included in all cases or may be included in specific cases, such as where the signs or symptoms of NAS are considered ambiguous.

Controlled-Release Formulations

Controlled-release formulations described herein are useful for all aspects and embodiments of methods provided herein. In some embodiments, controlled-release formulations described herein will degrade during a period of at least 4 days (e.g. 5 to 30 days) providing a slow "taper" release of opioid. Without being bound by theory, it is believed that such degradation of certain controlled-release formulations may serve to gradually wean an infant off from an opioid while avoiding symptoms of sudden withdrawal.

For example, a controlled release formulation is one described in PCT Publication Nos. WO 2005/117830, WO 2014/016428, and/or WO 2017/046384, each of which is incorporated herein by reference.

In some embodiments, any suitable controlled-release formulation may be used in the various aspects of the disclosure, as context allows. In some embodiments, a controlled release formulation, when administered to an infant, will release a dose of opioid active agent (e.g. maintain a therapeutic dosage) over a period of at least 4 days (e.g. 4 to 30 days, 4 to 25 days or 4 to 21 days), such as at least 5 days (e.g. 5 to 21 days or 5 to 18 days or 5 to 14 days). Appropriate controlled-release formulations will generally provide a tapering plasma opioid profile in the infant over such periods mentioned such that sudden withdrawal from the opioid is prevented and withdrawal symptoms reduced or minimized. Example of controlled release formulations are described in PCT Publication Nos. WO 2005/117830, WO 2014/016428, and/or WO 2017/046384, each of which is incorporated herein by reference.

Without being bound by theory, it is believed that in order to provide a suitable period of sustained release, a controlled-release formulation of and for use in all aspects of the current disclosure will have a half-life of at least 4 days. In some aspects of the current disclosure a half-life of a controlled release lipid formulation is about 4 days, 5 days or more (e.g. 4 days to 21 days; e.g. 4 days, 5 days, 6 days, 7 days, etc.). Such a half-life can be measured in vitro such as by injection of a small volume of controlled-release formulation into an excess of aqueous medium, such as phosphate buffered saline, measuring the concentration of active agent in the aqueous medium and plotting the release curve over time. Such a curve can then be curve-fitted to an logarithmic release to find the corresponding half-life. A similar test can be carried out in vivo, such as in rat, by injecting a small volume of controlled-release formulation into an animal, measuring the plasma concentration of active agent in blood samples taken over time and plotting the release curve. Such a curve can then be curve-fitted to a logarithmic release to find the corresponding half-life.

In some embodiments, a controlled-release formulation of and for use in all aspects of the current disclosure will typically have a half-life of at least 4 days (such as 4 to 21 days), preferably at least 5 days or at least 7 days. Without being bound by theory, it is believed that a very long half-life may be undesirable in order to avoid unnecessarily prolonged exposure of the infant to opioid agents. In some embodiments, a half-life is less than 30 days, such as less than 14 days or less than 10 days. Lipid controlled-release formulations disclosed herein have a half-life of about 5 days (e.g. 4 to 6 days).

Controlled-release formulations include lipid controlled-release formulations and polymer-based controlled-release formulations.

Any suitable lipid controlled-release formulation may be used in the methods and other aspects of the present disclosure. One suitable lipid controlled-release formulation comprises:

at least one neutral mono-, di- or tri-acyl lipid, and/or tocopherol;

optionally at least one phospholipid;

a solvent; and the at least one opioid.

Such components are described herein below and may be chosen from any of those indicated herein.

An effective type of lipid controlled-release formulation for use in all aspects of the present disclosure is a lipid controlled-release formulation such as the formulations disclosed in PCT Publication No. WO2005/117830 and related publications.

Lipid formulations comprising buprenorphine have been disclosed, such as in PCT Publication No. WO2014/016428. Additionally lipid formulations for treatment of withdrawal symptoms are currently approved in Australia and EU and marketed under the tradename Buvidal. However, the existing formulations, including the formulations disclosed in PCT Publication No. WO2014/016428 are not appropriate, nor approved, for treatment of NAS.

In one embodiment applicable to all aspects of the disclosure, the controlled-release formulation will be a non-liquid crystalline lipid formulation which forms at least one liquid crystalline phase upon exposure to an aqueous fluid. Such phase transitions are known from, for example, PCT Publication No. WO 2005/117830 and result in the formation of a high-viscosity non-lamellar (especially liquid crystalline or "L3-phase") self-assembled monolith when the precursor formulation absorbs water from an aqueous fluid such as a body fluid.

In some embodiments, a controlled-release formulation comprises:

i) at least one neutral diacyl lipid and/or a tocopherol;

ii) at least one phospholipid; and iii) at least one biocompatible organic solvent.

In some embodiments, a controlled-release formulation comprises:

i) at least one diacyl lipid, such as glycerol dioleate;

ii) at least one phospholipid; and iii) at least one biocompatible organic solvent.

In some embodiments, formulations described herein are in the form of low-viscosity mixtures, which may be molecular solutions or swollen L2 phase mixtures and are not liquid crystalline. Such formulations preferably form, or are capable of forming, non-lamellar (e.g. liquid crystalline or L3) phases upon exposure to aqueous fluid (e.g. in vitro or when injected into the body).

Components i) and ii) may be formulated in a wide range of proportions. The weight ratios of components i):ii) may thus be anything from about 5:95 right up to about 95:5. In some embodiments, a ratio of components i):ii) is from about 90:10 to about 20:80. In some embodiments, a ratio of components i):ii) is from about 85:15 to about 30:70. In some embodiments, a ratio of components i):ii) is about from 40:60 to about 80:20. In some embodiments, a ratio of components i):ii) is about 50:50. In some embodiments, a ratio of components i):ii) is from about 40:60 to about 60:40. In some embodiments, a ratio of components i):ii) is about 40:60. In some embodiments, a ratio of components i):ii) is about 45:55. In some embodiments, a ratio of components i):ii) is about 55:45. In some embodiments, a ratio of components i):ii) is about 60:40.

Components i) and ii) may be formulated in a wide range of proportions. The weight ratios of components i):ii) may thus be anything from 5:95 right up to 95:5. In some embodiments, a ratio of components i):ii) is from 90:10 to 20:80. In some embodiments, a ratio of components i):ii) is from 85:15 to 30:70. In some embodiments, a ratio of components i):ii) is from 40:60 to 80:20. In some embodiments, a ratio of components i):ii) is 50:50. In some embodiments, a ratio of components i):ii) is from 40:60 to 60:40. In some embodiments, a ratio of components i):ii) is 40:60. In some embodiments, a ratio of components i):ii) is 45:55. In some embodiments, a ratio of components i):ii) is 55:45. In some embodiments, a ratio of components i):ii) is 60:40.

In some embodiments, an amount of component i) in the controlled-release formulation is from about 10% to about 90%. In some embodiments, an amount of component i) in the controlled-release formulation is from about 18 to about 90%) by weight of the total formulation. In some embodiments, an amount of component i) in the controlled-release formulation is from about 10% to about 70% by weight of the total formulation. In some embodiments, an amount of component i) in the controlled-release formulation is from about 12% to about 40% by weight of the total formulation. In some embodiments, an amount of component i) in the controlled-release formulation is from about 12% to about 30% by weight of the total formulation. In some embodiments, an amount of component i) in the controlled release formulation is about 42.5% by weight of the formulation. In one embodiment, the absolute amount of component i) by weight is no less than the amount of component ii).

In some embodiments, an amount of component ii) in a controlled-release formulation is, for example, from about 8% to about 90% by weight of the total formulation. In some embodiments, an amount of component ii) in a controlled-release formulation is about. 18 to about 90% by weight of the total formulation. In some embodiments, an amount of component ii) in a controlled-release formulation is about 8% to about 70% by weight of the total formulation. In some embodiments, an amount of component ii) in a controlled-release formulation is about 10% to about 40% by weight of the total formulation. In some embodiments, an amount of component ii) in a controlled-release formulation is from about 10% to about 30% by weight of the total formulation. In some embodiments, an amount of component i) in the controlled release formulation is about 42.5% by weight of the formulation.

In some embodiments, an amount of component i) in the controlled-release formulation is from 10% to 90%. In some embodiments, an amount of component i) in the controlled-release formulation is from 18 to about 90%) by weight of the total formulation. In some embodiments, an amount of component i) in the controlled-release formulation is from 10% to 70% by weight of the total formulation. In some embodiments, an amount of component i) in the controlled-release formulation is from 12% to 40% by weight of the total formulation. In some embodiments, an amount of component i) in the controlled-release formulation is from 12% to 30% by weight of the total formulation. In some embodiments, an amount of component i) in the controlled release formulation is 42.5% by weight of the formulation. In one embodiment, the absolute amount of component i) by weight is no less than the amount of component ii).

In some embodiments, an amount of component ii) in a controlled-release formulation is, for example, from 8% to 90% by weight of the total formulation. In some embodiments, an amount of component ii) in a controlled-release formulation is 18 to 90% by weight of the total formulation. In some embodiments, an amount of component ii) in a controlled-release formulation is 8% to 70% by weight of the total formulation. In some embodiments, an amount of component ii) in a controlled-release formulation is 10% to 40% by weight of the total formulation. In some embodiments, an amount of component ii) in a controlled-release formulation is from 10% to 30% by weight of the total formulation. In some embodiments, an amount of component i) in the controlled release formulation is 42.5% by weight of the formulation.

In some embodiments, an amount of component iii) in a controlled-release formulation is at least sufficient to provide a mixture of injectable viscosity. The phase behaviour of lipid formulations may be analysed by techniques such as visual observation in combination with polarized light microscopy, nuclear magnetic resonance, x-ray or neutron diffraction, and cryo-transmission electron microscopy (cryo-TEM) to look for solutions, L2 or L3 phases, or liquid crystalline phases. Viscosity may be measured directly by standard means. As described above, an appropriate practical viscosity is that which can effectively be syringed and particularly sterile filtered. This will be assessed easily as indicated herein.

In some embodiments, a weight of solvent component iii) is from about 0.5 to about 50% of the total weight of the controlled-release formulation. In some embodiments, a weight of component iii) is from about 20 to about 40% by total weight of the formulation. In some embodiments, a weight of component iii) is from about 20 to about 38% by weight of the total formulation. In some embodiments, a weight of component iii) is from about 25 to about 35% by weight of the total formulation. In some embodiments, a weight of component iii) is about 30% by weight of the total formulation. In some embodiments, a weight of component iii) is from about 15 to about 45% by weight of the total formulation. In some embodiments, a weight of component iii) is from about 10 to about 30% by weight of the controlled-release formulation. In some embodiments, a weight of component iii) is from about 10 to about 40% by weight of the controlled-release formulation. In some embodiments, a weight of component iii) is about 10% by weight of the formulation. In some embodiments, a weight of component iii) is about from 5 to about 12% by total weight of the formulation.

In some embodiments, a weight of solvent component iii) is from 0.5 to 50% of the total weight of the controlled-release formulation. In some embodiments, a weight of component iii) is from 20 to 40% by total weight of the formulation. In some embodiments, a weight of component iii) is from 20 to 38% by weight of the total formulation. In some embodiments, a weight of component iii) is from 25 to 35% by weight of the total formulation. In some embodiments, a weight of component iii) is 30% by weight of the total formulation. In some embodiments, a weight of component iii) is from 15 to 45% by weight of the total formulation. In some embodiments, a weight of component iii) is from 10 to 30% by weight of the controlled-release formulation. In some embodiments, a weight of component iii) is from 10 to 40% by weight of the controlled-release formulation. In some embodiments, a weight of component iii) is 10% by weight of the formulation. In some embodiments, a weight of component iii) is from 5 to 12% by total weight of the formulation.

Component i)

In some embodiments, component "i)" as indicated herein comprises a diacyl lipid component comprising a polar "head" group and also two non-polar "tail" groups. Generally, the head and tail portions of the lipid will be joined by an ester moiety but this attachment may be by means of an ether, an amide, a carbon-carbon bond or other attachment. In some embodiments, polar head groups are "neutral" head groups, which are non-ionic. Examples include polyols such as glycerol, diglycerol and sugar moieties (such as inositol and glucosyl based moieties); and esters of polyols, such as acetate or succinate esters. In some embodiments, polar groups are glycerol and diglycerol, especially glycerol.

As indicated herein, "neutral" diacyl lipids are non-ionic lipids with two acyl groups, particularly acyl groups described herein. Diacyl glycerols form exemplary neutral diacyl lipids and include dioleoyl glycerol and dipalmitoleoyl glycerol. Dioleoyl glycerol, also known as glycerol dioleate (GDO) forms a particular example.

In some embodiments, diacyl glycerols of component i) comprise glycerol and two acyl chains as indicated herein.

In some embodiments, component i) comprises a diacyl lipid, e.g. diacyl glycerol. Such a lipid has two non-polar "tail" groups. This is preferable to the use of mono-acyl ("lyso") lipids because, without being bound by theory, mono-acyl lipids are typically less well tolerated in vivo. The two non-polar groups may have the same or a differing number of carbon atoms and may each independently be saturated or unsaturated. Examples of non-polar groups include C6-C32 alkyl and alkenyl groups, which are typically present as the esters of long chain carboxylic acids. These are often described by reference to the number of carbon atoms and the number of unsaturations in the carbon chain. Thus, CX:Z indicates a hydrocarbon chain having X carbon atoms and Z unsaturations. Examples particularly include myristoyl (C14:0), palmitoyl (C16:0), phytanoyl (C16:0), palmitoleoyl (C16:1), stearoyl (C18:0), oleoyl (C18:1), elaidoyl (C18:1), linoleoyl (C18:2), linolenoyl (C18:3), arachidonoyl (C20:4), behenoyl (C22:0) and lignoceroyl (C24:9) groups. In some embodiments, non-polar chains are based on the fatty acids of natural ester lipids, including caproic, caprylic, capric, lauric, myristic, palmitic, phytanic, palmitolic, stearic, oleic, elaidic, linoleic, linolenic, arachidonic, behenic or lignoceric acids, or the corresponding alcohols. In some embodiments, non-polar chains are palmitic, stearic, oleic and linoleic acids, particularly oleic acid. In one embodiment, component i) comprises components with C16 to C18 alkyl groups, particularly such groups having zero, one or two unsaturations (e.g. one or two double bonds). In some embodiments, component i) comprise at least 50% of components having such alkyl groups.

In some embodiments, a diacyl lipid, when used as all or part of component "i)", may be synthetic or may be derived from a purified and/or chemically modified natural sources such as vegetable oils. In some embodiments, component i) is or comprises mixtures of any number of diacyl lipids. In some embodiments, component i) is or comprises a diacyl glycerol (DAG). In some embodiments, component i) is or comprises glycerol dioleate (GDO). In one embodiment, component i) essentially consists of DAGs, e.g. a single DAG or a mixture of DAGs. An example is DAG comprising at least 50%, such as at least 80%, such as at least 90%, such as at least 93%, such as at least 94%, such as at least 95%, such as at least 96%, such as at least 97%, and even comprising substantially 100% GDO. An exemplary diacyl lipid is glycerol dioleate (GDO). Suitable GDO compositions may comprise at least 90% GDO, e.g. at least 93% GDO (e.g. 93 to 97% GDO). This may be at least 94% or at least 95%. A certain level of monoglycerides and triglycerides is inevitable in preparations of GDO. However, component a) of the controlled-release formulations of the present disclosure will typically contain no more than 10 wt % triacyl lipid (e.g. triglycerides). This may be no more than 8% (e.g. 2 to 8%) and more preferably no more than 6% (e.g. 3 to 6%).

Furthermore component a) of the controlled-release formulations of the present disclosure will typically contain no more than 5% monoacyl lipid (including monoglycerides). This may be no more than 4% (e.g. 0.5 to 4%) and more preferably no more than 3% (e.g. 1 to 3%).

In some embodiments, component b) of the controlled-release formulations of the present disclosure comprises at least 85% phosphatidylcholine (by dry weight). In some embodiments, component b) comprises at least 90% phosphatidylcholine. In some embodiments, component b) comprises from about 90 to about 98% phosphatidylcholine. In some embodiments, component b) comprises or at least 92% phosphatidylcholine. In some embodiments, component b) comprises from about. 92 to about 96% phosphatidylcholine.

In some embodiments, the total lipid component of the controlled-release formulations of the present disclosure will typically contain no more than 10% triacyl lipid (including triglycerides). This may be no more than 8% (e.g. 1 to 8%) and more preferably no more than 6% (e.g. 1.5 to 6%) triglycerides.

In some embodiments, the total lipid component of the controlled-release formulations of the present disclosure will typically contain no more than 5% monoacyl lipid (including monoglycerides). This may be no more than 4% (e.g. 0.25 to 4%) and more preferably no more than 3% (e.g. 0.5 to 3%) monoglycerides.

In some embodiments, purity of commercial GDO preparations is assessed by chromatography. For example, in some embodiments, mono-, di- and tri-glycerides are analysed by Size Exclusion Chromatography. Ph Eur 2.2.30 (area %). In some embodiments, fatty acids such as Linoleic Acid Content (%), are assessed by Gas Chromatography. Ph Eur 2.4.22. Similar methods can be applied to the measurement of lipid components indicated herein.

An alternative or additional class of compounds for use as all or part of component i) are tocopherols.

In some embodiments, a combination of constituents for component i) is a mixture of at least one DAG (e.g. at least one C16 to C18 DAG, such as GDO) with at least one tocopherol. Such mixtures include 2:98 to 98:2 by weight tocopherol:GDO, e.g. 10:90 to 90:10 tocopherol:GDO and especially 20:80 to 80:20 of these compounds. Similar mixtures of tocopherol with other DAGs are also suitable.

Component ii)

In some embodiments, component "ii)" is or comprises at least one phospholipid. As with component i), component ii) comprises a polar head group and at least one non-polar tail group. The difference between components i) and ii) lies principally in the polar group. The non-polar portions may thus suitably be derived from the fatty acids or corresponding alcohols considered above for component i). In particular C16 to C18 acyl groups having zero, one or two sites of unsaturation are highly suitable as moieties forming the non-polar group of the compounds of component ii). It will typically be the case that the phospholipid will contain two non-polar groups, although one or more constituents of this component may have one non-polar moiety. Where more than one non-polar group is present these may be the same or different.

Phospholipid polar "head" groups in aspects and embodiments disclosed herein include phosphatidylcholine (PC), phosphatidylethanolamine (PE), phosphatidylserine (PS) and phosphatidylinositol (PI). In some embodiments, component b) comprises at least 70% by weight of PC, PE or mixtures thereof. Phosphatidylcholine (PC) is generally used in embodiments disclosed herein. In some embodiments, component ii) comprises at least 50% PC by weight, e.g. at least 70% by weight of PC. In some embodiments disclosed herein at least 90% by weight of PC is used, e.g. at least 94%, at least 95%, at least 97% by weight of PC. In some embodiments, component ii) may consist essentially of PC.

A phospholipid may be derived from a natural source. Suitable sources of phospholipids include egg, heart (e.g. bovine), brain, liver (e.g. bovine) and plant sources including soybean.

In some embodiments, a suitable composition described herein comprises combination of components i) and ii) is GDO with PC, such as about 30 to about 48 wt % GDO, about 30 to about 48 wt % PC. In some embodiments, a composition comprises about 30 to about 48 wt % GDO, about 30 to about 48 wt % PC and about 5 to about 15 wt % ethanol.

In some embodiments, a suitable composition described herein comprises combination of components i) and ii) is GDO with PC, such as 30 to 48 wt % GDO, 30 to 48 wt % PC. In some embodiments, a composition comprises 30 to 48 wt % GDO, 30 to 48 wt % PC and 5 to 15 wt % ethanol.

In some embodiments, a composition described herein comprises about 35 to about 48 wt % GDO, about 35 to about 48 wt % PC. In some embodiments, a composition described herein comprises about 35 to about 48 wt % GDO, about 35 to about 48 wt % PC, about 7 to about 12 wt % EtOH, and about 0.05 to about 1 wt % of at least one opioid active agent. In some embodiments, a ratio of PC/GDO is from about 0.75 to about 1.2, e.g. about 0.85 to about 1.15 is suitable.

In some embodiments, a composition described herein comprises 35 to 48 wt % GDO, 35 to 48 wt % PC. In some embodiments, a composition described herein comprises 35 to 48 wt % GDO, 35 to 48 wt % PC, 7 to 12 wt % EtOH, and 0.05 to 1 wt % of at least one opioid active agent. In some embodiments, a ratio of PC/GDO is from about 0.75 to about 1.2, e.g. about 0.85 to about 1.15 is suitable.

In some embodiments, formulations described herein further comprise, in addition to amphiphilic components i) and ii), lipid-based pre-formulations of the disclosure may also contain additional amphiphilic components at relatively low levels. In some embodiments of the disclosure, a pre-formulation contains up to 10% (by weight of components i) and ii)) of a charged amphiphile, particularly an anionic amphiphile such as a fatty acid. Preferred fatty acids for this purpose include caproic, caprylic, capric, lauric, myristic, palmitic, phytanic, palmitolic, stearic, oleic, elaidic, linoleic, linolenic, arachidonic, behenic or lignoceric acids, or the corresponding alcohols.

Preferable fatty acids are palmitic, stearic, oleic and linoleic acids, particularly oleic acid. The formulations of the disclosure comprising diacyl lipids may also contain up to 10% by weight of an optional triacyl glycerol, such as those described herein.

Component iii)

Component "iii" of the preferred depot vehicle is a biocompatible (e.g. an oxygen containing) organic solvent. It is desirable that this solvent be tolerable to the subject and be capable of mixing with the aqueous fluid, and/or diffusing or dissolving out of the medicament into the aqueous fluid. Solvents having at least moderate water solubility are thus preferred.

In some embodiments, solvents suitable for use as component iii) include at least one solvent selected from alcohols, ketones, esters (including lactones), ethers, amides (including lactams) and sulphoxides. Examples of suitable alcohols include ethanol, isopropanol, benzylalcohol and glycerol formal. Monools are preferred to diols and polyols. Where diols or polyols are used, this is preferably in combination with an at least equal amount of monool or other preferred solvent. In some embodiments, e.g. when the active agent is an opioid, a prostacyclin or analogues thereof, or a peptide active agent, component iii) is ethanol and/or a polar solvent such as water and/or propylene glycol. Examples of solvents comprising ketones include acetone and propylene carbonate. Suitable ethers include diethylether, glycofurol, diethylene glycol monoethyl ether, dimethylisobarbide, and polyethylene glycols. Suitable esters include ethyl acetate, benzyl benzoate and isopropyl acetate and dimethyl sulphide is as suitable sulphide solvent. Suitable amides and sulphoxides include dimethylacetamide (DMA), n-methyl pyrrolidone (NMP), 2-pyrrolidone and dimethylsulphoxide (DMSO). Less preferred solvents include dimethyl isosorbide, tetrahydrofurfuryl alcohol, diglyme and ethyl lactate. In some embodiments, component iii) is or comprises ethanol (EtOH).

In some embodiments, component iii) comprises a single solvent, (e.g. EtOH), or a mixture including another suitable solvent. The solvent or solvent mixture is important because it provides a means for controlling the ease of injection, as the solvent or solvent mixture may be used to control the viscosity of the controlled-release formulation.

In one particular embodiment of the present disclosure, applicable to all aspects including the formulations of the disclosure, such formulations may be:

In some embodiments, the present disclosure provides a lipid controlled-release formulation comprising:
- a) about 30 to about 50 wt % of at least one diacyl glycerol;
- b) about 30 to about 50 wt % of at least one phosphatidylcholine;
- c) about 5 to about 15 wt % ethanol;
- d) about 0.05 to about 0.5 wt % buprenorphine.

In some embodiments, a weight percentage of buprenorphine is calculated as the free base moiety weight of buprenorphine.

In some embodiments, the present disclosure provides a lipid controlled-release formulation comprising:
- a) 30 to 50 wt % of at least one diacyl glycerol;
- b) 30 to 50 wt % of at least one phosphatidylcholine;
- c) 5 to 15 wt % ethanol;
- d) 0.05 to 0.5 wt % buprenorphine.

Unless otherwise specified, a weight percentage of buprenorphine is calculated as the free base moiety weight of buprenorphine.

In some embodiments of such a lipid controlled-release formulation, the proportion of the sum of the weights of components a) and b) to the total weight of the formulation is at least 50% (e.g. about 50 to about 95%, about 60 to about 80%, such as 50 to 95%, 60 to 80%). That is to say, the amount by weight of all lipid components in the lipid controlled-release formulation as a proportion of the total weight of the lipid controlled-release formulation may be at least 50% (e.g. 50 to 95%, such as 60 to 80%).

In some embodiments, of a lipid controlled-release formulation, comprising components a) to d), the ratio of components a):b) is from about 40:60 to about 60:40, such as about 45:55 to about 55:45 (e.g. 40:60, 45:55, 50:50, 55:45, or 60:40). A ratio of a):b) of about 50:50 will be one embodiment.

Component a)

Component a) is a subset of component i) described above and relates to the specific lipid controlled-release formulations of the present disclosure where component i) relates to broader formulations which may be used in the methods of the disclosure.

In some embodiments, component a) comprises a diacyl glycerol or mixture thereof as described herein above for component i). Component a) will generally comprise at least 50% by weight glycerol dioleate (GDO). Component a) may comprise at least 50% (e.g. 50 to around 99%) GDO, such as at least 70%, at least 80%, at least 85% or at least 90% GDO. Component a) may consist essentially of GDO (e.g. not less than 93%, 95%, 97% by weight GDO). In some embodiments component a) comprises GDO, having a fatty acid composition of at least 93% oleic acid (18:1), as determined in accordance with method C, 2.4.22 (Composition of fatty acids by gas chromatography), European Pharmacopoeia 9.0.

Component b)

Component b) is a subset of component ii) described above and relates to the specific lipid controlled-release formulations of the present disclosure where component ii) relates to broader formulations which may be used in the methods of the disclosure.

In some embodiments, component b) comprises a phosphatidylcholine or mixture thereof as described herein above for component ii). Component b) may comprise at least 50% (e.g. 50 to around 99%) soy phosphatidylcholine, such as at least 70%, at least 80%, at least 85% or at least 90% soy phosphatidylcholine. Component b) may consist essentially of soy phosphatidylcholine (e.g. not less than 94% by weight phosphatidylcholine).

Component c)

Component c) is a subset of component iii) described above and relates to the specific lipid controlled-release formulations of the present disclosure where component iii) relates to broader formulations which may be used in the methods of the disclosure.

In some embodiments, component c) of the lipid controlled-release formulations comprising components a) to d) above comprises ethanol in an amount of about 5 to about 15% by weight of components a) to d). In some embodiments, this may be about 5 to about 12 wt % or about 8 to about 10% by weight. Amounts about 10 wt % are appropriate.

In some embodiments, component c) of the lipid controlled-release formulations comprising components a) to d) above is ethanol in an amount of 5 to 15% by weight of components a) to d). In some embodiments, this may be 5 to 12 wt % or 8 to 10% by weight.

Component d)

In some embodiments, component d) of the lipid controlled-release formulations comprising components a) to d) above will be buprenorphine in an amount of about 0.05 to about 5% by weight of total lipid controlled-release formulation, e.g. d) is about 0.05 to about 4.2% by weight, d) is about 0.05 to about 0.55% by weight. In some embodiments d) is 0.05 to 0.5% by weight.

"Buprenorphine" as used herein will be buprenorphine or any buprenorphine salt but will be calculated as the free molecule for the purposes of wt %. The same calculation will apply to buprenorphine and other opioids used in all aspects of the disclosure.

In some embodiments, component d) of the lipid controlled-release formulations comprising components a) to d) above, is present such that the concentration of buprenorphine (free base) is selected from the group consisting of 0.5, 1, 2, 3, 4 and 5 mg/mL. In some embodiments, a concentration of buprenorphine in formulations described herein is selected from the group consisting of 0.5, 1, 2, 3, and 4 mg/mL In some embodiments, a concentration of buprenorphine in formulations described herein is selected from the group consisting of 1, 2, 3 and 4 mg/mL. In some embodiments, a concentration of buprenorphine in formulations described herein is selected from the group consisting of 1, 2 and 3 mg/mL. In some embodiments, a concentration of buprenorphine in formulations described herein is selected from the group consisting of 0.5, 1, and 2 mg/mL.

Exemplary embodiments include:

In some embodiments, a formulation corresponds to one of the following formulations, A to F:

| Formulation | A | B | C | D | E | F |
| --- | --- | --- | --- | --- | --- | --- |
| | | | Content (mg/mL) | | | |
| Buprenorphine (free base) | 0.5 ± 0.1 | 1.0 ± 0.2 | 2.0 ± 0.3 | 3.0 ± 0.5 | 4.0 ± 0.5 | 5.0 ± 0.5 |
| Glyceryl dioleate | 450 ± 50 | 450 ± 50 | 450 ± 50 | 450 ± 50 | 450 ± 50 | 450 ± 50 |
| Phosphatidylcholine | 450 ± 50 | 450 ± 50 | 450 ± 50 | 450 ± 50 | 450 ± 50 | 450 ± 50 |
| Ethanol | 100 ± 50 | 100 ± 50 | 100 ± 50 | 100 ± 50 | 100 ± 50 | 100 ± 50 |

In some embodiments, a formulation corresponds to one of the following formulations, wherein the concentration of buprenorphine (free base) is selected from the group consisting of 0.5, 1, 2, 3, 4 and 5 mg/mL (amounts selected according to the density of the formulation, which is estimated at around 0.95 g/mL).

| Buprenorphine mg/mL | 0.5 | 1 | 2 | 3 | 4 | 5 |
| --- | --- | --- | --- | --- | --- | --- |
| | | | Content (mg/g) | | | |
| Buprenorphine (free base) | 0.5 ± 0.1 | 1.0 ± 0.2 | 2.0 ± 0.3 | 3.0 ± 0.5 | 4.0 ± 0.5 | 5.0 ± 0.5 |
| Glyceryl dioleate | 450 ± 50 | 450 ± 50 | 450 ± 50 | 450 ± 50 | 450 ± 50 | 450 ± 50 |
| Phosphatidylcholine | 450 ± 50 | 450 ± 50 | 450 ± 50 | 450 ± 50 | 450 ± 50 | 450 ± 50 |
| Ethanol | 100 ± 50 | 100 ± 50 | 100 ± 50 | 100 ± 50 | 100 ± 50 | 100 ± 50 |

In some embodiments, a formulation corresponds to one of the following formulations, wherein the concentration of buprenorphine (free base) is selected from the group consisting of 0.5, 1, 2, 3, and 4 mg/mL.

| Buprenorphine mg/mL | 0.5 | 1 | 2 | 3 | 4 |
| --- | --- | --- | --- | --- | --- |
| | | Content (mg/g) | | | |
| Buprenorphine (free base) | 0.5 ± 0.1 | 1.0 ± 0.2 | 2.0 ± 0.3 | 3.0 ± 0.5 | 4.0 ± 0.5 |
| Glyceryl dioleate | 450 ± 50 | 450 ± 50 | 450 ± 50 | 450 ± 50 | 450 ± 50 |
| Phosphatidylcholine | 450 ± 50 | 450 ± 50 | 450 ± 50 | 450 ± 50 | 450 ± 50 |
| Ethanol | 100 ± 50 | 100 ± 50 | 100 ± 50 | 100 ± 50 | 100 ± 50 |

In some embodiments, a formulation corresponds to one of the following formulations, wherein the concentration of buprenorphine (free base) is selected from the group consisting of 1, 2, 3, and 4 mg/mL.

| Buprenorphine mg/mL | 1 | 2 | 3 | 4 |
| --- | --- | --- | --- | --- |
| | | Content (mg/g) | | |
| Buprenorphine (free base) | 1.0 ± 0.2 | 2.0 ± 0.3 | 3.0 ± 0.5 | 4.0 ± 0.5 |
| Glyceryl dioleate | 450 ± 50 | 450 ± 50 | 450 ± 50 | 450 ± 50 |
| Phosphatidylcholine | 450 ± 50 | 450 ± 50 | 450 ± 50 | 450 ± 50 |
| Ethanol | 100 ± 50 | 100 ± 50 | 100 ± 50 | 100 ± 50 |

In some embodiments, a formulation corresponds to one of the following formulations, wherein the concentration of buprenorphine (free base) is selected from the group consisting of 2, 3, and 4 mg/mL.

| Buprenorphine mg/mL | 2 | 3 | 4 |
| --- | --- | --- | --- |
| | Content (mg/g) | | |
| Buprenorphine (free base) | 2.0 ± 0.3 | 3.0 ± 0.5 | 4.0 ± 0.5 |
| Glyceryl dioleate | 450 ± 50 | 450 ± 50 | 450 ± 50 |
| Phosphatidylcholine | 450 ± 50 | 450 ± 50 | 450 ± 50 |
| Ethanol | 100 ± 50 | 100 ± 50 | 100 ± 50 |

In some embodiments, a formulation corresponds to one of the following formulations G to L. In each formulation, the amounts of any component may vary by ±10% of the value stated. The total of any other components, such as water, preservatives or lipid impurities will generally be no more than 100 mg/mL, preferably no more than 80 mg/mL.

The density of the lipid formulation may vary depending on the amount of ethanol, and is estimated to be 0.95 g/mL at room temperature. The density of the lipid formulation may increase over time due to evaporation of ethanol. Amounts below for Formulations G to L assume 0.95 g/mL but may be corrected within the indicated ranges to give convenient mg/mL concentrations and thus convenient dosing volumes.

| Formulation | G | H | I | J | K | L |
|---|---|---|---|---|---|---|
| Content (mg/g) | | | | | | |
| Buprenorphine (base) | 0.53 ± 10% | 1.05 ± 10% | 2.11 ± 10% | 3.16 ± 10% | 4.21 ± 10% | 5.26 ± 10% |
| Glyceryl dioleate | 449 ± 10% | 449 ± 10% | 449 ± 10% | 448 ± 10% | 448 ± 10% | 447 ± 10% |
| Phosphatidylcholine | 449 ± 10% | 449 ± 10% | 449 ± 10% | 448 ± 10% | 448 ± 10% | 447 ± 10% |
| Ethanol | 100 ± 10% | 100 ± 10% | 100 ± 10% | 100 ± 10% | 100 ± 10% | 100 ± 10% |

In some embodiments of the above-mentioned formulations the phosphatidylcholine (PC) is soybean phosphatidylcholine (soybean PC).

In some embodiments, the formulation may be a formulation selected from the group consisting of formulations G to K above.

In some embodiments, the formulation may be a formulation selected from the group consisting of formulations H to K above.

In some embodiments, the formulation may be a formulation selected from the group consisting of formulations I to K above.

The following formulations I) to VI) form separate specific formulation embodiments, as well as being appropriate formulations for use in all other aspects of the disclosure:

I)
    a) 45±8 (e.g. 45±5) wt % glycerol dioleate,
    b) 45±8 (e.g. 45±5) wt % phosphatidylcholine, e.g. soybean PC,
    c) 10±5 wt % (e.g. 10±2 wt %) ethanol, and
    d) 0.05±0.01 (e.g. 0.05±0.005) wt % buprenorphine;

II)
    a) 45±8 (e.g. 45±5) wt % glycerol dioleate,
    b) 45±8 (e.g. 45±5) wt % phosphatidylcholine, e.g. soybean PC,
    c) 10±5 wt % (e.g. 10±2 wt %) ethanol, and
    d) 0.1±0.02 (e.g. 0.1±0.01) wt % buprenorphine;

III
    a) 45±8 (e.g. 45±5) wt % glycerol dioleate,
    b) 45±8 (e.g. 45±5) wt % phosphatidylcholine, e.g. soybean PC,
    c) 10±5 wt % (e.g. 10±2 wt %) ethanol, and
    d) 0.2±0.03 (e.g. 0.2±0.02) wt % buprenorphine;

IV)
    a) 45±8 (e.g. 45±5) wt % glycerol dioleate,
    b) 45±8 (e.g. 45±5) wt % phosphatidylcholine, e.g. soybean PC,
    c) 10±5 wt % (e.g. 10±2 wt %) ethanol, and
    d) 0.3±0.06 (e.g. 0.3±0.03) wt % buprenorphine;

V)
    a) 45±8 (e.g. 45±5) wt % glycerol dioleate,
    b) 45±8 (e.g. 45±5) wt % phosphatidylcholine, e.g. soybean PC,
    c) 10±5 wt % (e.g. 10±2 wt %) ethanol, and
    d) 0.4±0.08 (e.g. 0.4±0.04) wt % buprenorphine; and VI)
    a) 45±8 (e.g. 45±5) wt % glycerol dioleate,
    b) 45±8 (e.g. 45±5) wt % phosphatidylcholine, e.g. soybean PC,
    c) 10±5 wt % (e.g. 10±2 wt %) ethanol, and
    d) 0.5±0.1 (e.g. 0.5±0.05) wt % buprenorphine.

Pre Filled Containers

In some embodiments, lipid controlled-release formulations of the present disclosure may be supplied in the form of a pre-filled sealed container, such as sealed or septum-capped vial from which an appropriate volume may be withdrawn for administration according to the dose to be administered. Such a dose may be dependent upon the weight of the infant and/or the severity of NAS/NOWS symptoms (e.g. a NAS score) as discussed herein. A pre-filled vial (or sealed container) containing a lipid controlled-release formulation as described herein thus forms a further aspect of the disclosure.

Such a pre-filled container/vial will typically contain a total dose of not more than 2,500 µg of buprenorphine (e.g. 75 to 2,000 µg, such as 100 to 1,500 µg, such as 250 to 1,000 µg) as herein throughout, where the buprenorphine is in the form of a salt, the amount is calculated as free buprenorphine.

Such a pre-filled container/vial will typically contain a total volume of lipid controlled-release formulation of not more than 1.25 mL or no more than 1 mL, such as no more than 0.5 mL, such as 0.25 to 0.75 mL. This may correspond to the injected amount, being for example of 0.1-1.0 mL or 0.15-1 mL, such as 0.15-0.5 mL, such as 0.2-0.5 mL. Alternatively the amount may be slightly greater (e.g. 0.1 to 0.25 mL greater) to allow for some remaining in the container after withdrawal of the dose. In some embodiments the container is a pre-filled syringe.

Other Controlled-Release Formulations

In an alternative embodiment applicable to all technically compatible aspects of the present disclosure (especially the methods of the disclosure), the lipid controlled-release formulation may comprise:
    x) a lipid controlled-release matrix comprising at least 50% triacyl lipids; and
    y) at least one oxygen containing organic solvent.

Triacyl lipids in this embodiment may be triacyl glycerols (triglycerides).

The oxygen containing solvent component y) in this embodiment will typically be as defined herein for component iii) above.

In some embodiments, the active agent component may be an opioid or opioid salt, as discussed herein, particularly buprenorphine or a salt thereof. The lipid controlled-release formulation may thus additionally comprise:

Component x), where component x) typically forms 10% to 70% by weight of the total lipid controlled-release formulation in this embodiment. This may be 15% to 64% or 20 to 50% by weight.

In lipid component x), at least 50% of the lipids are formed of triacyl lipids. Thus, generally 50% to 100% (such as at least 80%), preferably 60 to 90% or 60% to 95%, more preferably 70 to 90% of said lipid controlled release matrix (component x)) is formed of triacyl lipids. Component x) may consist essentially of triacyl lipids (e.g. be 95% or more triacyl lipids).

Certain other controlled-release formulations, such as those containing the use of a biodegradable polymer may also be used in any compatible aspect of the disclosure. Various depot systems comprising polymers, such as poly-lactic acid, polyglycolic acid and/or polylactate/glycolate copolymers are well known in the art.

Suitable systems have been shown to provide syringe able, in-situ forming, solid biodegradable implants (e.g. for animals—U.S. Pat. No. 4,938,763), or solvent-based pre-cursor formulations such as those described in U.S. Pat. No. 10,022,367, see e.g. the examples. An injection is made of the polymer or solvent-based formulation in liquid form (e.g. in solution) which subsequently "cures" to form the implant in-situ. In order to form the polymer-based implant, a thermoplastic system is applied, comprising the steps of: dissolving a non-reactive polymer in biocompatible solvent to form a liquid, placing the liquid within the subject (e.g. by injection) and allowing the solvent to dissipate to produce the solid implant. Similarly a solvent-based formulation including one or more active ingredient(s) may upon injec-tion in a subject form an implant. Related methods may be used in the case of an in-situ forming and syringe able formulation which is polymer based for a biodegradable implant. Such implants will utilise biodegradable polymers such as polyesters (e.g. polylactate or polylactate-co-glyco-late polymers).

Another sustained-release preparation that is free from an organic solvent has been produced (U.S. Pat. No. 6,113,943) comprising of: a hydrolysed polymer of lactic acid having a weight-average molecular weight from about 25,000 to 60,000 and a polydispersity of about 1.2 to about 4.0 and a physiologically active substance which is released over a period of at least around 5 months through preparation.

The disclosure thus provides a method of the present disclosure wherein the controlled-release formulation is polymer-based.

The disclosure further provides a method of the present disclosure wherein the controlled-release formulation com-prises:

a biotolerable polymer;

a solvent; and at least one opioid, such a buprenorphine.

Opioids used and formulated in the present disclosure may be morphine, methadone or buprenorphine, either as the free drug or as pharmaceutically acceptable salts such as those known in the art.

In some embodiments, the present disclosure relates to buprenorphine and salts thereof.

In all cases herein, where a mg/mL or mg/g value is indicated for an opioid this relates to the free drug or the corresponding amount where a salt is used. Thus, for example, 0.50 mg/g in a formulation may correspond to 0.50 mg of buprenorphine (molecular weight: 467.6 g/mol) in a gram of formulation or to 0.539 mg of buprenorphine hydrochloride (molecular weight: 504.1 g/mol).

The lipid controlled-release formulations contained in all appropriate aspects and embodiments herein will be flow-able, injectable fluids. Where the lipid controlled-release formulation forms a non-lamellar (e.g. liquid crystalline) depot for release of the active agent, this non-lamellar formulation will typically be formed upon exposure to an aqueous fluid (e.g. a body fluid). The lipid controlled-release formulation within the device will typically be in a non-liquid crystalline form such as a molecular solution or dilute L2 phase. The lipid controlled-release formulation will typically form a liquid crystalline phase such as a normal or reversed cubic or hexagonal phase upon exposure to an aqueous environment (e.g. to body fluids).

The viscosity of the controlled-release formulations of and used in all embodiments of the present disclosure should be such that they can reasonably be injected using pressures and forces generated by hand or by a small injection device, e.g. an auto-injector. Generally, the controlled-release for-mulations will be low to moderate viscosity, in the range 100 to 1000 mPas at 25° C. (e.g. 200 to 900 mPas, such as 300 to 900, such as 300 to 600, such as 300-500 or 400 to 900 mPas at 25° C.).

Additional advantages aspects and embodiments dis-closed herein may include a fast onset giving immediate (e.g. within 15 minutes) relief from symptoms of NAS. As plasma levels are steadily tapered in the infant, the with-drawal symptoms may continue to be relieved while reliance on the opioid is gradually diminished. Current treatments including medicaments can lead to constipation which the aspects and embodiments disclosed herein also have poten-tial to reduce.

Suitable ranges of dosage will depend upon the infant weight, the duration of release of the controlled-release formulation and may depend upon the severity of the NAS/NOWS symptoms (e.g. NAS score) upon initiation.

In one embodiment, applicable to all aspects, a single dose of 25-1000 µg buprenorphine per kg bodyweight is contemplated. This dose may be 25-500 µg/kg (e.g. 43-500 µg/kg), such as 47-250 µg/kg, or about 50 µg/kg and applies to the methods of the disclosure, to the formulations and the use of such formulations.

Where a second dose is used, this second dose may be in the same ranges. Where a second dose is used, the total of the two doses may be in the same ranges.

In one embodiment, applicable to all aspects, the present disclosure provides for a single administration of a volume of 0.1-1 mL, such as 0.1-0.5 mL of the controlled-release formulation as described herein, e.g. 0.15-1 mL of the lipid controlled-release formulation composition. This volume may be 0.1-0.5 mL, such as 0.15-0.5 mL This applies to the methods of the disclosure, to the formulations and the use of such formulations as described herein. Where a second dose is used, this second dose may conform to the same ranges.

EXEMPLARY EMBODIMENTS

Preferred embodiments of the method aspect of the pres-ent disclosure include:

1. A lipid controlled-release formulation comprising:
    a) about 30 to about 50 wt % (e.g. 30-50 wt %) of at least one diacyl glycerol;
    b) about 30 to about 50 wt % (e.g. 30-50 wt %) of at least one phosphatidylcholine;
    c) about 5 to about 15 wt % (e.g. 5-15 wt %) ethanol;
    d) about 0.05 to about 0.5 wt % (e.g. 0.05-0.5 wt %) buprenorphine.

2. The lipid controlled-release formulation of embodi-ment 1, wherein the ratio of components a):b) is about 40:60 to about 60:40.

3. The lipid controlled-release formulation of embodiment 1, wherein the ratio of components a):b) is about 45:55 to about 55:45.

4. The lipid controlled-release formulation of any one of embodiments 1 to 3, wherein the ratio of components a):b) is about 50:50.

4. The lipid controlled-release formulation of any one of embodiments 1 to 4, wherein the sum of the weights of components a) and b) is at least 50% of the total weight of the formulation.

5. The lipid controlled-release formulation of any one of embodiments 1 to 4, wherein the sum of the weights of components a) and b) is about 50 to about 95% of the total formulation.

6. The lipid controlled-release formulation of any one of embodiments 1 to 5 wherein component a) comprises at least 85% by weight glycerol dioleate.

7. The lipid controlled-release formulation of any one of embodiments 1 to 6 wherein component b) comprises at least 85% by weight phosphatidylcholine.

8. The lipid controlled-release formulation of any one of embodiments 1 to 7 wherein the concentration of buprenorphine (calculated free base) is about 0.5 to about 5 mg/mL.

9. The lipid controlled-release formulation of any one of embodiments 1 to 8 wherein the concentration of buprenorphine (calculated free base) is selected from the group consisting of 0.5, 1.0, 1.5, 2.0, 2.5, 3.0, 3.5, 4.0, 4.5, and 5.0 mg/mL.

10. A lipid controlled-release formulation selected from the group consisting of:

I)
   a) 45±5 wt % glycerol dioleate,
   b) 45±5 wt % phosphatidylcholine,
   c) 10±5 wt % ethanol, and
   d) 0.05±0.01 wt % buprenorphine;

II)
   a) 45±5 wt % glycerol dioleate,
   b) 45±5 wt % phosphatidylcholine,
   c) 10±5 wt % ethanol, and
   d) 0.1±0.02 wt % buprenorphine;

III
   a) 45±5 wt % glycerol dioleate,
   b) 45±5 wt % phosphatidylcholine,
   c) 10±5 wt % ethanol, and
   d) 0.2±0.03 wt % buprenorphine;

IV)
   a) 45±5 wt % glycerol dioleate,
   b) 45±5 wt % phosphatidylcholine,
   c) 10±5 wt % ethanol, and
   d) 0.3±0.05 wt % buprenorphine;

V)
   a) 45±5 wt % glycerol dioleate,
   b) 45±5 wt % phosphatidylcholine,
   c) 10±5 wt % ethanol, and
   d) 0.4±0.05 wt % buprenorphine; and VI)
   a) 45±5 wt % glycerol dioleate,
   b) 45±5 wt % phosphatidylcholine,
   c) 10±5 wt % ethanol, and
   d) 0.5±0.05 wt % buprenorphine.

11. The lipid controlled-release formulation of any one of embodiments 1 to 9, wherein the formulation corresponds to one of the following formulations, A to F:

| Formulation | A | B | C | D | E | F |
|---|---|---|---|---|---|---|
| | Content (mg/g) | | | | | |
| Buprenorphine (free base) | 0.5 ± 0.1 | 1.0 ± 0.2 | 2.0 ± 0.3 | 3.0 ± 0.5 | 4.0 ± 0.5 | 5.0 ± 0.5 |
| Glyceryl dioleate | 450 ± 50 | 450 ± 50 | 450 ± 50 | 450 ± 50 | 450 ± 50 | 450 ± 50 |
| Phosphatidylcholine | 450 ± 50 | 450 ± 50 | 450 ± 50 | 450 ± 50 | 450 ± 50 | 450 ± 50 |
| Ethanol | 100 ± 50 | 100 ± 50 | 100 ± 50 | 100 ± 50 | 100 ± 50 | 100 ± 50 |

12. The lipid controlled-release formulation of any one of embodiments 1 to 7 wherein the formulation corresponds to one of the following formulations, G to L:

| Formulation | G | H | I | J | K | L |
|---|---|---|---|---|---|---|
| | Content (mg/g) | | | | | |
| Buprenorphine (free base) | 0.53 ± 10% | 1.05 ± 10% | 2.11 ± 10% | 3.16 ± 10% | 4.21 ± 10% | 5.26 ± 10% |
| Glyceryl dioleate | 449 ± 10% | 449 ± 10% | 449 ± 10% | 448 ± 10% | 448 ± 10% | 447 ± 10% |
| Phosphatidylcholine | 449 ± 10% | 449 ± 10% | 449 ± 10% | 448 ± 10% | 448 ± 10% | 447 ± 10% |
| Ethanol | 100 ± 10% | 100 ± 10% | 100 ± 10% | 100 ± 10% | 100 ± 10% | 100 ± 10% |

13. The lipid controlled-release formulation of any one of embodiments 1 to 12 wherein the phosphatidylcholine is soybean phosphatidylcholine.

14. The lipid controlled-release formulation of any one of embodiments 1 to 13 wherein the formulation provides in vitro and/or in vivo release of buprenorphine with a half-life of not less than 4 days.

15. The lipid controlled-release formulation of embodiment 14, wherein the formulation provides in vitro and/or in vivo release of buprenorphine with a half-life of about 4 to about 14 days.

16. The lipid controlled-release formulation of any of embodiments 1 to 15 for use in the treatment of neonatal opioid withdrawal syndrome (NOWS) in an infant.

17. The lipid controlled-release formulation for use as recited in embodiment 16, wherein said treatment comprises administration of 25-1,000 µg/kg, or 43-500 µg/kg of buprenorphine (calculated as free base) to said infant.

18. The lipid controlled-release formulation for use as recited in embodiment 16 or embodiment 17 wherein 0.11-1 mL of the controlled-release formulation according to any one of embodiments 1 to 11 is administered to said infant.

19. The lipid controlled-release formulation for use as recited in embodiment 18 wherein 0.1-0.5 mL of the controlled-release formulation according to any one of embodiments 1 to 12 is administered to said infant.

20. A pre-filled vial containing a formulation as recited in any one of embodiments 1 to 14.

21. The pre-filled vial as recited in embodiment 20 containing a total dose of not more than 2,000 µg of buprenorphine (calculated as buprenorphine free base).

22 The pre-filled vial as recited in embodiment 21 containing a total dose of about 50 to about 2,000 µg of buprenorphine (calculated as buprenorphine free base).

23. The pre-filled vial as recited in any one of embodiments 20 to 22, wherein the pre-filled vial comprises about 1 mL or less of the controlled-release formulation.

24. The pre-filled vial as recited in embodiment 22 containing about 0.1 to about 0.5 mL of the controlled-release formulation.

25. A method for the treatment of neonatal abstinence syndrome (NAS) in a human infant in need thereof, said treatment involving the steps of:
administering a controlled-release formulation containing a dose of at least one opioid to said infant;
wherein said controlled-release formulation provides a therapeutically effective amount of opioid for at least 4 days following administration.

26. The method of embodiment 25 wherein said controlled-release formulation provides a therapeutically effective amount of opioid for at least 5 days following administration.

27. The method of embodiment 25 or embodiment 26 wherein said neonatal abstinence syndrome is neonatal opioid withdrawal syndrome (NOWS).

28. The method of any one of embodiments 25 to 27 comprising no more than two administrations of said controlled-release formulation.

29. The method of any one of embodiments 25 to 27 comprising only a single administration of said controlled-release formulation, said administration being by subcutaneous injection.

30. The method of any one of embodiments 25 to 29 wherein said infant is in need of pharmacological treatment for NAS according to at least one NAS scoring methodology.

31. The method of embodiment 30 wherein said at least one NAS scoring methodology is selected from the group consisting of the Finnegan scoring method, the modified Finnegan scoring method, the Lipsitz scoring method, the Ostrea scoring method, the Rivers scoring method, the Neonatal Intensive Care Unit Network Neurobehavioral Scale, the neonatal narcotic withdrawal index, the neonatal withdrawal inventory and the MOTHERS NAS scale.

32. The method of any one of embodiments 25 to 30 wherein said infant is in need of treatment for NAS according to the Finnegan scoring method and/or the modified Finnegan scoring method.

33. The method of any one of embodiments 25 to 32 wherein said method is supplemented by non-pharmacological methods including low stimulation, parental engagement and/or breast-feeding.

34. The method of any one of embodiments 25 to 33 wherein the controlled-release formulation is a lipid controlled-release formulation.

35. The method of any one of embodiments 25 to 34 wherein the controlled-release formulation comprises:
at least one neutral mono-, di- or tri-acyl lipid, and/or tocopherol;
optionally at least one phospholipid;
a solvent; and
the at least one opioid.

36. The method according to embodiment 35 wherein the controlled-release formulation forms, or is capable of forming, a liquid crystalline phase structure on exposure to an aqueous fluid.

37. The method of any one of embodiments 25 to 36 wherein the controlled-release formulation is a lipid controlled release formulation as recited in any one of embodiments 1 to 14.

38. The method of any one of embodiments 25 to 37 wherein the at least one opioid is methadone, buprenorphine, or morphine.

39. The method of any one of embodiments 25 to 38 wherein the at least one opioid is buprenorphine.

40. The method of any one of embodiments 25 to 39 wherein the at least one opioid is buprenorphine and said dose is selected on the basis of the bodyweight of said infant at an amount of 33-500 µg buprenorphine per kg bodyweight.

41. The method of embodiment 40, wherein the dose is about 43 to about 500 µg/kg.

42. The method of embodiment 41, wherein the dose is about 47 to about 250 µg/kg.

43. The method of embodiment 42, wherein the dose is about 50 µg/kg.

44. The method of any one of embodiments 25 to 43 wherein the at least one opioid is buprenorphine and an amount of buprenorphine in the controlled-release formulation is from about 50 to about 2,500 µg.

45. The method of any one of embodiments 25 to 44 wherein said controlled-release formulation provides a therapeutic concentration of opioid for a duration of at least 4 days.

46. The method of embodiment 45, wherein said controlled-release formulation provides a therapeutic concentration of opioid for a duration of 5 days.

47. The method of embodiment 45, wherein said controlled-release formulation provides a therapeutic concentration of opioid for a duration of 5 to 30 days.

48. The method of any one of embodiments 25 to 47 wherein said controlled-release formulation is administered by injection of a volume of about 0.11 to about 1 mL.

49. The method of any one of embodiments 25 to 47 wherein said controlled-release formulation is administered by injection of a volume of about 0.1 to about 0.5 mL.

50. The method of any one of embodiments 25 to 48 wherein said controlled-release formulation is administered by injection of a volume of about 0.15 to about 0.5 mL.

51. The method of any one of embodiments 25 to 50, wherein said controlled-release formulation is one of the following formulations, A to F:

| Formulation | A | B | C | D | E | F |
|---|---|---|---|---|---|---|
| | | | Content (mg/g) | | | |
| Buprenorphine (free base) | 0.5 ± 0.1 | 1.0 ± 0.2 | 2.0 ± 0.3 | 3.0 ± 0.5 | 4.0 ± 0.5 | 5.0 ± 0.5 |
| Glyceryl dioleate | 450 ± 50 | 450 ± 50 | 450 ± 50 | 450 ± 50 | 450 ± 50 | 450 ± 50 |
| Phosphatidylcholine | 450 ± 50 | 450 ± 50 | 450 ± 50 | 450 ± 50 | 450 ± 50 | 450 ± 50 |
| Ethanol | 100 ± 50 | 100 ± 50 | 100 ± 50 | 100 ± 50 | 100 ± 50 | 100 ± 50 |

52. The method of any one of embodiments 25 to 50 wherein said controlled-release formulation is one of the following formulations, G to L:

| Formulation | G | H | I | J | K | L |
|---|---|---|---|---|---|---|
| | | | Content (mg/g) | | | |
| Buprenorphine (free base) | 0.53 ± 10% | 1.05 ± 10% | 2.11 ± 10% | 3.16 ± 10% | 4.21 ± 10% | 5.26 ± 10% |
| Glyceryl dioleate | 449 ± 10% | 449 ± 10% | 449 ± 10% | 448 ± 10% | 448 ± 10% | 447 ± 10% |
| Phosphatidylcholine | 449 ± 10% | 449 ± 10% | 449 ± 10% | 448 ± 10% | 448 ± 10% | 447 ± 10% |
| Ethanol | 100 ± 10% | 100 ± 10% | 100 ± 10% | 100 ± 10% | 100 ± 10% | 100 ± 10% |

53. The method of embodiments 51 or 52, wherein said phosphatidylcholine is soybean phosphatidylcholine.

54. A method for the treatment of neonatal abstinence syndrome (NAS) in a human infant in need thereof, said treatment involving the steps of:

administering a controlled-release formulation containing a dose of at least one opioid to said infant;

wherein said controlled-release formulation provides a therapeutically effective amount of opioid for at least 4 days following administration.

55. The method of embodiment 54 wherein said controlled-release formulation provides a therapeutically effective amount of opioid for at least 5 days following administration.

56. The method of embodiment 54 or 55 wherein said neonatal abstinence syndrome is neonatal opioid withdrawal syndrome (NOWS).

57. The method of any of embodiments 54 to 56 comprising no more than two administrations of said controlled-release formulation.

58. The method of any of embodiments 54 to 57 comprising only a single administration of said controlled-release formulation, said administration being by subcutaneous injection.

59. The method of any of embodiments 54 to 58 wherein said infant is in need of pharmacological treatment for NAS according to at least one NAS scoring methodology.

60. The method of any of embodiments 54 to 59 wherein said infant is in need of pharmacological treatment for NAS according to at least one NAS scoring methodology selected from the group consisting of the Finnegan scoring method, the modified Finnegan scoring method, the Lipsitz scoring method, the Ostrea scoring method, the Rivers scoring method, the Neonatal Intensive Care Unit Network Neurobehavioral Scale, the neonatal narcotic withdrawal index, the neonatal withdrawal inventory and the MOTHERS NAS scale.

61. The method of any of embodiments 54 to 60 wherein said infant is in need of treatment for NAS according to the Finnegan scoring method and/or the modified Finnegan scoring method.

62. The method of any of embodiments 54 to 61 wherein said method is supplemented by non-pharmacological methods including low stimulation, parental engagement and/or breast-feeding.

63. The method of any of embodiments 54 to 62 wherein the controlled-release formulation is a lipid controlled release formulation.

64. The method of any of embodiments 54 to 63 wherein the controlled-release formulation comprises:

at least one neutral mono-, di- or tri-acyl lipid, and/or tocopherol;

optionally at least one phospholipid;

a solvent; and said opioid.

65. The method according to embodiment 64 wherein said the controlled-release formulation forms, or is capable of forming, at least one liquid crystalline phase structure on exposure to an aqueous fluid.

66. The method of any of embodiments 54 to 56 wherein controlled-release formulation is a lipid controlled release formulation as described herein including in the attached claims.

67. The method of any of embodiments 54 to 66 wherein said opioid is methadone, buprenorphine, morphine.

68. The method of any of embodiments 54 to 67 wherein said opioid is buprenorphine.

69. The method of any of embodiments 54 to 68 wherein said opioid is buprenorphine and wherein said dose is selected on the basis of the bodyweight of said infant at an amount of 25-500 µg buprenorphine per kg bodyweight, typically 43-500 µg/kg, such as 47-250, or about 50 µg/kg.

70. The method of any of embodiments 54 to 69 wherein said opioid is buprenorphine and wherein said dose is in the range of 50 to 2,500 µg.

71. The method of any of embodiments 54 to 70 wherein said controlled-release formulation provides a therapeutic concentration of opioid for a duration of at least 4 days, such as 5 days, such as 5 to 30 days 72. The method of any of claims embodiments 54 to 71 wherein said controlled-release formulation is administered by injection of a volume of 0.1-1 mL, such as 0.1-0.5 mL, such as 0.15-0.5 mL.

73. The method of any of claims embodiments 54 to 56 wherein said controlled-release formulation is one of the following formations, G to L:

| Formulation | G | H | I | J | K | L |
|---|---|---|---|---|---|---|
| | | | Content (mg/g) | | | |
| Buprenorphine (base) | 0.53 ± 10% | 1.05 ± 10% | 2.11 ± 10% | 3.16 ± 10% | 4.21 ± 10% | 5.26 ± 10% |
| Glyceryl dioleate | 449 ± 10% | 449 ± 10% | 449 ± 10% | 448 ± 10% | 448 ± 10% | 447 ± 10% |
| Phosphatidylcholine | 449 ± 10% | 449 ± 10% | 449 ± 10% | 448 ± 10% | 448 ± 10% | 447 ± 10% |
| Ethanol | 100 ± 10% | 100 ± 10% | 100 ± 10% | 100 ± 10% | 100 ± 10% | 100 ± 10% |

75. The method of any embodiments 25-73, wherein the controlled-release formulation is administered subcutaneously.

76. The method of embodiment 75, wherein a controlled release formulation is administered to a subcutaneous tissue selected from the buttocks, the thigh, the abdomen, and the upper arm.

77. The method of embodiment 75, wherein a controlled release formulation is administered to a subcutaneous tissue in the buttocks.

In a further aspect, the present disclosure provides for a controlled-release formulation containing a dose of at least one opioid for use in the treatment of NAS. In various embodiments, such formulation for use is for use in any of the embodiments indicated herein including embodiments 1 to 73 above.

EXAMPLES

Example 1—Formulations

The following lipid, solvent and opioid components are weighed into a vial and mixed by end-over-end rotation at room temperature until a homogeneous mixture is generated (e.g. rotation for 48 hours).

| Formulation | G | H | I | J | K | L |
|---|---|---|---|---|---|---|
| | | | Content (mg/g) | | | |
| Buprenorphine (base) | 0.53 | 1.05 | 2.11 | 3.16 | 4.21 | 5.26 |
| Glyceryl dioleate | 449.7 | 449.5 | 448.9 | 448.4 | 447.9 | 447.4 |
| Soybean phosphatidylcholine | 449.7 | 449.5 | 448.9 | 448.4 | 447.9 | 447.4 |
| Ethanol | 100 | 100 | 100 | 100 | 100 | 100 |

Mixtures are sterile filtered prior to transfer into sealed vials. At administration, an appropriate volume is withdrawn for injection according to the weight of the subject, the selected dose per kg and the buprenorphine content of the respective formulation.

Example 2—Administration

A neonate with suspected NOWS is subjected to the Finnegan Neonatal Abstinence Scoring Tool (FNAST) every 3-4 hours beginning at 2 hours after birth for a minimum of 96 hours. Where the infant has two consecutive scores of 9 or greater, a single injected dose of controlled-release formulation is provided according to the highest score attained and the weight of the subject. The infant is monitored and provided with an Eat, Sleep, Console regime for at least 96 hours following the administration. Where a FNAST score is maintained below 9 for at least 3 consecutive scores after 96 hours following administration, discharge from hospital is considered.

Example 3—Pharmacokinetic (PK) Evaluation

A pediatric formulation is being developed for the treatment of Neonatal Opioid Withdrawal Syndrome (NOWS). The formulation is based on BUP (buprenorphine) concentrations (0.5 (G), 1 (H) and 2 (I) mg/mL). The formulations G, H and I were delivered ready to use in glass vials. Prior to administration, the test items were visually inspected according to the three criteria clarity, homogenous and non-precipitated.

The formulations were compared to a comparative formulation (CF) of 6.25 mg/ml buprenorphine (0.66 BUP, 43.67 GDO, 43.67 SPC, 12.00 EtOH).

The study was performed in 24 Male SPF Sprague-Dawley rats (SD-M) from Janvier labs (Cedex, France). Four (4) extra animals were available for replacement purposes. An acclimatization period of 5 days was allowed before dosing.

The animals were divided into two cohorts, which were dosed on separate, consecutive, days. At the day before dosing, the 24 animals were weighed (not recorded) and animals were given individual numbers from 1 to 24. All rats were marked by identification numbers in the ear. The identification was punched earmarks. The randomization and identification were performed according to an internal marking system. On the day of dosing, the animals were allocated to treatment groups according to the following scheme:

| Group No. | Animal no. |
| --- | --- |
| 1 | 1, 8, 9, 16, 17, 24 |
| 2 | 2, 7, 10, 15, 18, 23 |
| 3 | 3, 6, 11, 14, 19, 22 |
| 4 | 4, 5, 12, 13, 20, 21 |

Study Design

| Group No | No. of animals | Formulation | Route of administration | Conc of BUP (mg/mL) | Dose (mg/Rat) | Dose Volume (mL/Rat) |
| --- | --- | --- | --- | --- | --- | --- |
| 1 | 6 | G | subcutane | 0.5 | 0.05 | 0.1 |
| 2 | 6 | H | subcutane | 1 | 0.1 | 0.1 |
| 3 | 6 | I | subcutane | 2 | 0.2 | 0.1 |
| 4 | 6 | CF | subcutane | 6.25 | 0.625 | 0.1 |

The PK profile of BUP with these parameters was evaluated in groups 1-3 in this study. Group 4 is a control group with a formulation with a known pharmacokinetic.

The animals were administered according to standard procedure. The day of dosing was designated Day 0. The study specific administration procedures are described below:

Body weights were recorded prior to administration.

Actual dose volumes were calculated based on the most recent body weight data.

Test items were visually inspected prior to administration and an acceptable appearance and injectability were verified.

Animals were anesthetized using isofluran, and the site of injection was shaved prior to administration.

Dosing was performed using a 1-mL Luer-lock syringe and a 25-mm 23G needle. One syringe and one needle for each group and day were used.

Animals were administrated by a subcutaneous injection in the fat tissue between the scapulae of the rats.

The weight of each syringe was determined before and after dosing. The dose was determined from the weight of the injected material, which is the difference between weight of a syringe before and after dosing and was compared to the nominal dose (dose volume).

All animals were inspected in connection with blood sampling, and any clinical observation, e.g. signs of ill health or behavioural changes, were documented. Extended observations were performed approximately 12 hours post dosing.

Pharmacokinetic Sample Collection and Analysis
Sample Collection

Blood for pharmacokinetic analysis was collected pre-dose, and at 1 hour, 6 hours, 24 hours (1 day), 48 hours (2 days), 96 hours (4 days), 168 hours (7 days), 264 hours (11 days) and 336 hours (14 days) after dosing. Actual time of collection were calculated by the difference between the actual time of collection and the time of dosing. The acceptable time ranges for blood collection were ±5 minutes (1 hour and 6 hours), ±2 hours (24 hours and 48 hours), ±6 hours (96 hours to 336 hours). A blood volume of 0.25 mL was collected into EDTA-treated test tubes (BD Micro-tainer® K2E, 365975, OneMed) at each sampling time point by sub-lingual bleeding. The samples were placed on ice (or at approximately +5° C.) immediately after collection and centrifuged (approximately 1500×g, at 5° C. for 10 min) within 60 minutes. Plasma was transferred into properly labeled 0.5-mL propylene test tubes (Eppendorf Safe lock tubes, Fisher Scientific) and stored below −70° C. until transportation on ice to WorldWide Clinical Trials, Austin Texas, US. The samples were delivered with a treatment scheme, including study number, rat number and blood sampling time points. The analysis of BUP in plasma was performed at WorldWide Clinical Trials, US, using LC-MS/MS method. The range of quantitation was 0.200 to 50.0 ng/mL for buprenorphine based on the analysis of 25.0 µL of plasma.

Pharmacokinetic Analysis

Prior to the pharmacokinetic analysis, plasma concentrations below the lower limit of quantification (LLOQ) were set to 0, if occurring before the first quantifiable sample and after the quantifiable range of the individual plasma profile. Plasma values below LLOQ within the quantifiable range were also set as 0. The nominal times were used in the pharmacokinetic calculations. The pharmacokinetic analysis was performed on the bioanalytic data using WinNonlin pharmacokinetic software, version 8.1 (Pharsight Corp., Mountain View, CA, USA). Non-Compartmental Analysis was performed on each individual data set. Individual and mean plasma concentration profiles were plotted as function of time.

The following primary parameters were determined according to the Study Plan:

| Abbreviation | Description |
| --- | --- |
| $C_{max}$ | The maximum plasma concentration observed; estimated directly from the data |
| $t_{max}$ | Time at which $C_{max}$ occurs; estimated directly from the data |
| $AUC_{last}$ | Area under the plasma concentration-time curve from time 0 to the last quantifiable time point using the linear up log down calculation method (linear trapezoidal rule when data concentration data is increasing and logarithmic trapezoidal rule when data is decreasing). |
| $AUC_{24\,h}$ | AUC during the first 24 hours (initial exposure) |
| $AUC_{0-th}$ | Area under the plasma concentration-time curve from time 0 to time t hours, e.g. $AUC_{96}$ means from time 0 to 96 hours |

Pharmaceutical Analysis of Test Items

After preparation of the test items (formulations G, H, I and CF), aliquots to be used for pharmaceutical analysis were stored at ≤−15° C.

Doses

Administered dose volumes and doses, both individual and means within treatment groups, are presented in Table 1.

TABLE 1

Body weight, dose and dose volume by treatment group

| Treatment Group | Test Item (formulation) | Animal No | Body Weight[1] (g) | Dose of BUP (mg/rat) | Dose Volume (mL/rat) |
| --- | --- | --- | --- | --- | --- |
| 1 | G | Rat 01 | 310 | 0.0522 | 0.104 |
| | | Rat 08 | 320 | 0.0475 | 0.0951 |
| | | Rat 09 | 320 | 0.0507 | 0.101 |
| | | Rat 16 | 320 | 0.0533 | 0.107 |

TABLE 1-continued

Body weight, dose and dose volume by treatment group

| Treatment Group | Test Item (formulation) | Animal No | Body Weight[1] (g) | Dose of BUP (mg/rat) | Dose Volume (mL/rat) |
| --- | --- | --- | --- | --- | --- |
| | | Rat 17 | 330 | 0.0507 | 0.101 |
| | | Rat 24 | 320 | 0.0496 | 0.0993 |
| 2 | H | Rat 02 | 300 | 0.0982 | 0.0982 |
| | | Rat 07 | 300 | 0.104 | 0.104 |
| | | Rat 10 | 330 | 0.103 | 0.103 |
| | | Rat 15 | 330 | 0.0972 | 0.0972 |
| | | Rat 18 | 330 | 0.0993 | 0.0993 |
| | | Rat 23 | 340 | 0.106 | 0.106 |
| 3 | I | Rat 03 | 320 | 0.213 | 0.107 |
| | | Rat 06 | 330 | 0.211 | 0.106 |
| | | Rat 11 | 320 | 0.205 | 0.102 |
| | | Rat 14 | 320 | 0.203 | 0.101 |
| | | Rat 19 | 320 | 0.219 | 0.110 |
| | | Rat 22 | 330 | 0.207 | 0.103 |
| 4 | CF | Rat 04 | 330 | 0.628 | 0.101 |
| | | Rat 05 | 310 | 0.661 | 0.106 |
| | | Rat 12 | 320 | 0.615 | 0.0984 |
| | | Rat 13 | 310 | 0.635 | 0.102 |
| | | Rat 20 | 320 | 0.655 | 0.105 |
| | | Rat 21 | 330 | 0.675 | 0.108 |

[1]The body weight of each animal was recorded on Day 0, prior to administration of the formulation.

All animals received a dose within 10% from the nominal dose and therefore nominal doses were used in the pharmacokinetic analyses.

Clinical Observations

All rats showed minor pharmacological effects of BUP, such as behavioral depression (staring eyes and dazed facial expressions, unsteady gait and slow reaction to auditory, tactile stimuli, and stereotyped behavior of motor responses (repetitive, invariant, and seemingly without purpose or goal), they recovered within 24 hours after dosing. At approximately 5 hours post dose, animal no 13 in treatment group 4 (CF), was unexpectedly found dead, which may be due to gastroparesis a well-known pharmacological effect of BUP.

All animals gained weight, with no obvious difference between animals of different treatment groups, except for three rats treated with CF, that initially showed a slight decrease compared to the other animals.

Bioanalysis

Analysis of BUP was performed according to method test method ATM-2530, WorldWide Clinical Trials.

Pharmacokinetic Evaluation

In this study, the PK parameters were compared between each test group (G, H, and I) and the control group CF. The plasma concentrations are shown in FIGS. 1-3 and the mean plasma concentrations of buprenorphine disclosed in Table 2.

Figure 2:
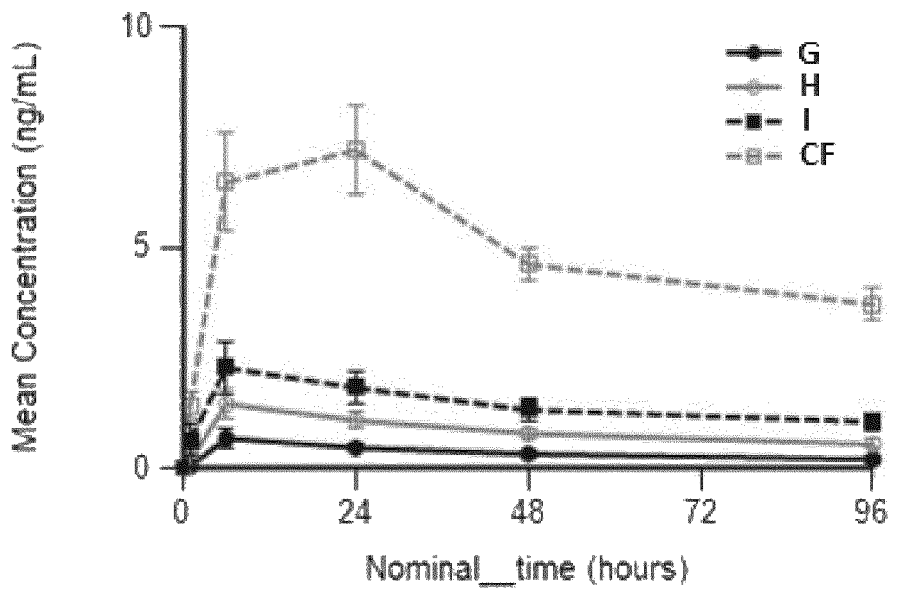
FIG. 2 shows mean Plasma Concentrations of BUP in Animals of Treatment Groups 1-4; hours 0-96 (Semi-log Scale)
Figure 3:
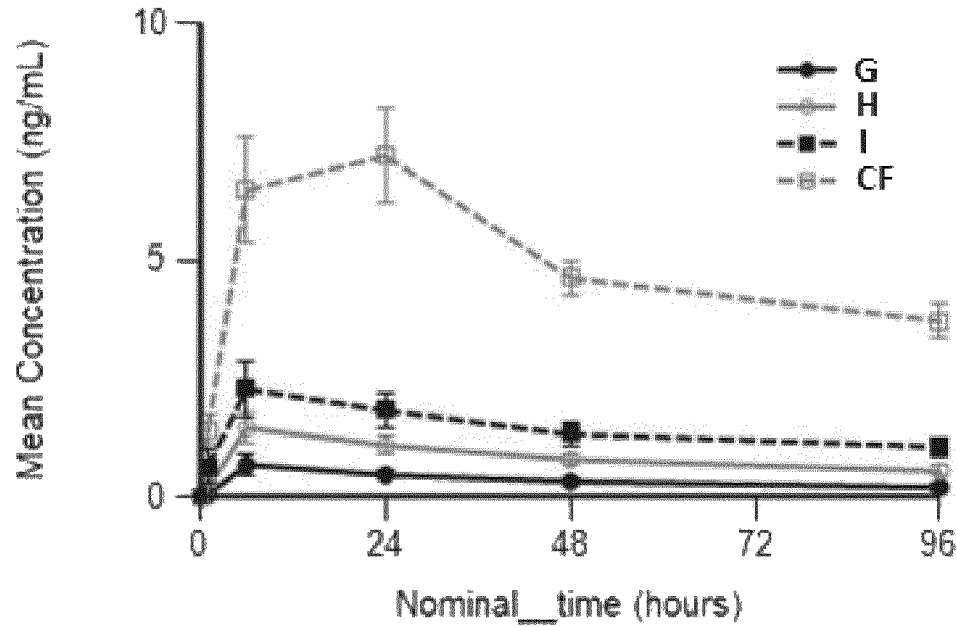
FIG. 3 shows mean Plasma Concentrations of BUP in Animals of Treatment Groups 1-4; hours 0-96 (Semi-log Scale)

Mean plasma BUP concentrations of the treatment groups are illustrated in FIGS. 1-3. Many of the measured plasma samples post-dose were below the LLOQ.

BUP was rapidly absorbed into the circulation following subcutaneous (SC) administration, and the absorption continued with quantifiable concentrations (above LLOQ=0.200 ng/mL) throughout at least 96 h for all 4 doses investigated, except for one rat in the group 1. The last timepoint for quantifiable concentrations was extended in a stepwise manner with increasing dose. More specifically, the duration of plasma concentration above LLOQ was 4 days for 0.5 mg/mL, 7 days for 1.0 mg/mL and 11-14 days for 2.0 mg/mL. For the control group, 2048BUP-J (6.25 mg/mL), quantifiable concentrations were measured throughout the study duration of 14 days.

TABLE 2

Primary PK parameters determined from plasma
concentrations of BUP by treatment group

| Treatment group | Formulation | Animal No | $t_{max}$ (hour) | $C_{max}$ (ng/mL) | $AUC_{last}$ (ng*h/mL) | $AUC_{96\,h}$ (ng*h/mL) | $AUC_{24\,h}$ (ng*h/mL) |
|---|---|---|---|---|---|---|---|
| 1 | G | N | 6 | 6 | 6 | 6 | 6 |
| | | Mean | 6.00 | 0.682 | 33.2 | 34.2 | 12.0 |
| | | SD | 0.00 | 0.243 | 10.5 | 8.88 | 3.74 |
| 2 | H | N | 6 | 6 | 6 | 6 | 6 |
| | | Mean | 6.00 | 1.46 | 114 | 81.0 | 26.9 |
| | | SD | 0.00 | 0.357 | 13.5 | 8.83 | 5.83 |
| 3 | I | N | 6 | 6 | 6 | 6 | 6 |
| | | Mean | 6.00 | 2.28 | 250 | 139 | 44.4 |
| | | SD | 0.00 | 0.570 | 27.2 | 26.2 | 10.5 |
| 4 | CF | N | 5 | 5 | 5 | 5 | 5 |
| | | Mean | 16.8 | 7.53 | 866 | 481 | 143 |
| | | SD | 9.86 | 0.785 | 62.2 | 13.3 | 13.6 |

Pharmacokinetic Parameters

The pharmacokinetic parameters of BUP are presented in Table 2.

The plasma concentrations of BUP generated after SC administration of the different test items reached maximum levels ($C_{max}$) at within 24 h. There were no significant differences found between $C_{max}$-values of each test group compared to the $C_{max}$-values of the control group (CF). After $C_{max}$ was reached, the concentrations declined in all groups to concentrations that were below LLOQ at the end of the study. The exposure of BUP during the first four days of the study, measured as $AUC_{96\,h}$, was determined to mean±SD values of 34.2±8.88, 81.0±8.83, 139±26.2 and 481±13.3 ng/mL*h in treatment groups G, H, I and CF, as disclosed in table 2. The initial release of BUP, during the first 24 hours were approximately 20%, which are signs of prolonged release PK profiles. The ratios of the test group (CF) were similar or slightly above the ratio of the control group.

The apparent half-life of BUP was determined to between 3 and 4 days, with no apparent difference between the treatment groups and the control group.

The comparative statistics in the current study was performed on dose- or exposure-normalized values when applicable. In line with the results described above, the statistical analysis (t-test) gave no significant difference in PK parameters between each test group compared to the control group.

All plasma profiles showed a prolonged release of BUP. The duration of plasma concentration above LLOQ (0.200 ng/mL) was 4 days for 0.05 mg/rat (G), 7 days for 0.1 mg/rat (H) and 11-14 days for 0.2 mg/rat (I). For the control group, CF (0.625 mg/rat), quantifiable concentrations were measured throughout the study duration of 14 days.

The exposure was found to be dose proportional between concentrations of 0.05 to 0.625 mg/rat. $C_{max}$ was also dose proportional within the same dose range and occurred at 6 hours for concentrations 0.05, 0.1 and 0.2 mg/rat and at 6-24 hours for 0.625 mg/rat. The results demonstrate that also the low doses tested had a prolonged release of BUP over at least 4 days.

Comparative Example 1—NAS Lipsitz Scoring Checklist

The 11 typical clinical signs of NAS used in the Lipsitz scoring method include these stated as follows:

Tremors: involuntary muscle activity of limbs which are rhythmical and normally of equal amplitude, including seizure on the rare occasion.

Irritability: excessive crying, high pitched and with no apparent reason. Inconsolable even after normal comforting measures.

Exaggerated Moro startle reflex even when examined at rest.

Loose, frequent, watery stools which may also be explosive with or without a water ring. Ignore 'breast milk' stools.

Varying degrees of muscle stiffness or rigidity.

Skin abrasions on elbows, heels or other pressure points. Ignore extremities frequently rubbed against bed linens and diaper rash.

Respiratory rate where infant is tachypneic or if breathing is laboured or retractions are present. Count respirations for sixty seconds when the infant is calm or asleep by touch or direct visualization of the chest and/or abdomen.

Repetitive sneezing may be a sign of autonomic nervous system dysregulation.

Repetitive yawning may represent alterations in autonomic nervous system regulation.

Projectile or forceful vomiting or right after baby is fed. Vomiting not necessarily related to burping and occurs frequently during feeding.

Fever >38° C. (>100.4° F.) unrelated to infant being overdressed or because of an infection.

Comparative Example 2—Modified Finnegan's Scoring Checklist

The following clinical signs of NAS used in the modified Finnegan's scoring method include these stated as follows:

Crying (excessive or continuous)
Lack of sleep
Hyperactive Moro reflex
Tremors
Increased muscle tone
Excoriation (e.g. on the chin, knees, elbows, toes, or nose)
Myoclonic jerks
Generalized convulsions
Increased sweating
Hypothermia
Frequent yawning (e.g. 3-4 times per scoring interval)
Mottling
Nasal stiffness
Sneezing (e.g. 3-4 times per scoring interval)
Nasal flaring
Increased respiratory rate (e.g. 60 breaths/minute)

Excessive sucking

Poor feeding

Regurgitation

Projective vomiting

Loose or watery stool.

Comparative Example 3: Methodology to
Determine Dosage Based on a NAS Scoring
Method Assuming a Finnegan neonatal abstinence scoring method is used, the short-acting opioid (morphine sulphate) will be started at a dose corresponding to the highest score if the infant has 2 consecutive scores ≥9. After that dose of morphine sulphate administered will depend on the subsequent Finnegan scores. The initial dose of morphine sulphate will be continued every 3-4 hours with feeds. Once the NAS score falls below 9 for 48 hours, start weaning the infant off the dose by 0.02 mg every 24 hours until discontinued. Infant may be discharged when removed form morphine for 24 hours with a score <9. The maximum interval for NAS scoring and morphine dosing is 4 hours while on treatment.

When using the long-acting opioid (e.g. methadone) a starting dose of 0.3 mg po q 12 hours (range of 0.3-0.6 mg po q12 hours depending upon severity of signs) is administered, which is increased by 0.3 mg if scores ≥9 after the first dose, and subsequently increased by 0.05-0.2 mg if scores are still ≥9 after 4 scheduled doses. Infants may be discharged home when scores are <9 for 24-48 hours on a stable methadone dose. However should the infant be somnolent, does not rouse spontaneously for feeds, or has abnormal eye movements, discontinue methadone immediately and continue scoring. If scores approach 7 or greater, restart methadone at lower dose corresponding to the number of hours that no methadone dose has been administered.

The invention claimed is:

1. A method for the treatment of neonatal abstinence syndrome (NAS) in a human infant in need thereof, said treatment comprising a step of:

administering a controlled-release formulation containing a dose of at least one opioid to said infant;

wherein said controlled-release formulation provides a therapeutically effective amount of the at least one opioid for at least 4 days following administration;

wherein the at least one opioid is buprenorphine, and wherein the controlled-release formulation is a lipid controlled-release formulation comprising:

a) about 30 to about 50 wt % of at least one diacyl glycerol;

b) about 30 to about 50 wt % of at least one phosphatidylcholine;

c) about 5 to about 15 wt % ethanol; and d) about 0.05 to about 0.5 wt % buprenorphine.

2. The method of claim 1, wherein said controlled-release formulation provides a therapeutically effective amount of buprenorphine for at least 5 days following administration.

3. The method of claim 1, wherein said neonatal abstinence syndrome is neonatal opioid withdrawal syndrome (NOWS).

4. The method of claim 1, further comprising administering a second dose of buprenorphine to the infant.

5. The method of claim 1, wherein said infant is in need of pharmacological treatment for NAS according to at least one NAS scoring methodology.

6. The method of claim 5, wherein said at least one NAS scoring methodology is selected from the group consisting of the Finnegan scoring method, the modified Finnegan scoring method, the Lipsitz scoring method, the Ostrea scoring method, the Rivers scoring method, the Neonatal Intensive Care Unit Network Neurobehavioral Scale, the neonatal narcotic withdrawal index, the neonatal withdrawal inventory and the MOTHERS NAS scale.

7. The method of claim 6, wherein said infant is in need of treatment for NAS according to the Finnegan scoring method and/or the modified Finnegan scoring method.

8. The method of claim 7, wherein said method is supplemented by non-pharmacological methods including low stimulation, parental engagement and/or breast-feeding.

9. The method of claim 1, wherein the controlled-release formulation is a lipid controlled-release formulation.

10. The method according to claim 1, wherein the controlled-release formulation forms, or is capable of forming, a liquid crystalline phase structure on exposure to an aqueous fluid.

11. The method of claim 1, wherein the dose of the buprenorphine is selected on the basis of the bodyweight of said infant at an amount of 33-500 µg buprenorphine per kg bodyweight.

12. The method of claim 1, wherein the amount of buprenorphine in the controlled-release formulation is from about 50 µg to about 2,500 µg.

13. The method of claim 1, wherein the controlled-release formulation is administered subcutaneously.

14. The method of claim 13, wherein a controlled-release formulation is administered to a subcutaneous tissue selected from the buttocks, the thigh, the abdomen, and the upper arm.

* * * * *